United States Patent
Ohashi et al.

(10) Patent No.: US 11,179,125 B2
(45) Date of Patent: Nov. 23, 2021

(54) MEDICAL IMAGE PROCESSING APPARATUS, X-RAY DIAGNOSIS APPARATUS, AND MEDICAL IMAGE PROCESSING METHOD

(71) Applicant: CANON MEDICAL SYSTEMS CORPORATION, Otawara (JP)

(72) Inventors: Shumpei Ohashi, Otawara (JP); Yoshiaki Iijima, Nasushiobara (JP); Kunio Shiraishi, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 40 days.

(21) Appl. No.: 16/394,591

(22) Filed: Apr. 25, 2019

(65) Prior Publication Data

US 2019/0328345 A1    Oct. 31, 2019

(30) Foreign Application Priority Data

Apr. 25, 2018  (JP) .............................. JP2018-084517

(51) Int. Cl.
  *G06K 9/00*  (2006.01)
  *A61B 6/00*  (2006.01)
  *G06T 5/50*  (2006.01)

(52) U.S. Cl.
  CPC ............ *A61B 6/487* (2013.01); *A61B 6/4441* (2013.01); *A61B 6/466* (2013.01); *A61B 6/481* (2013.01);
(Continued)

(58) Field of Classification Search
  CPC ......... A61B 6/481; A61B 6/504; A61B 6/486; A61B 6/5205; A61B 5/026; A61B 5/489; G06T 2207/10116; G06T 2207/10081; G06T 2207/30104; G06T 2207/20221; G06T 2210/41; G06T 7/38; H04N 5/32; A61N 2005/1061; A61N 2005/1062
  See application file for complete search history.

(56) References Cited

U.S. PATENT DOCUMENTS 4,543,604 A * 9/1985 Grosse ................. H04N 5/3205
                                                           378/98.12
4,618,976 A * 10/1986 Haendle ............... H04N 5/3205
                                                           348/E5.089
(Continued)

FOREIGN PATENT DOCUMENTS

JP  4-364677   12/1992
JP  6-292085   10/1994
(Continued)

*Primary Examiner* — Shervin K Nakhjavan
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured to sequentially obtain X-ray images. The processing circuitry is configured to sequentially generate average images by using the obtained plurality of X-ray images, in parallel to the obtainment of the X-ray images. The processing circuitry is configured to sequentially generate difference images by performing a difference calculating process between the X-ray images and the average images, in parallel to the obtainment of the X-ray images and the generation of the average images.

19 Claims, 12 Drawing Sheets

(52) U.S. Cl.
CPC ............ *A61B 6/504* (2013.01); *A61B 6/5217* (2013.01); *G06T 5/50* (2013.01); *G06T 2207/30101* (2013.01)

(56) References Cited

U.S. PATENT DOCUMENTS

| | | | | |
|---|---|---|---|---|
| 4,636,850 | A * | 1/1987 | Stewart | H04N 5/3205 348/E5.089 |
| 5,161,178 | A * | 11/1992 | Honda | H04N 5/3205 348/E5.089 |
| 5,233,989 | A * | 8/1993 | Honda | G06T 5/50 600/425 |
| 5,285,786 | A | 2/1994 | Fujii | |
| 5,467,380 | A * | 11/1995 | De Jonge | H04N 5/21 348/E5.077 |
| 8,064,986 | B2 * | 11/2011 | Profio | A61B 6/481 600/425 |
| 8,761,540 | B2 * | 6/2014 | Yang | G06T 11/008 382/275 |
| 2003/0048935 | A1 * | 3/2003 | Keren | A61B 6/481 382/130 |
| 2004/0079232 | A1 * | 4/2004 | Groh | A61B 6/4441 96/1 |
| 2005/0054916 | A1 * | 3/2005 | Mostafavi | A61B 6/504 600/427 |
| 2006/0029285 | A1 * | 2/2006 | Hein | G06T 5/002 382/260 |
| 2007/0009080 | A1 * | 1/2007 | Mistretta | G06T 11/006 378/4 |
| 2008/0051648 | A1 * | 2/2008 | Suri | A61B 6/5235 600/407 |
| 2008/0137935 | A1 * | 6/2008 | Spahn | G06T 5/50 382/132 |
| 2009/0022262 | A1 * | 1/2009 | Ohishi | A61B 6/504 378/4 |
| 2009/0252397 | A1 * | 10/2009 | Kuwabara | G06T 5/20 382/132 |
| 2010/0020933 | A1 * | 1/2010 | Topfer | H04N 5/3205 378/98.11 |
| 2011/0148928 | A1 * | 6/2011 | Gopalakrishnan | A61B 6/5288 345/643 |
| 2012/0321156 | A1 * | 12/2012 | Waechter-Stehle | A61B 6/5288 382/130 |
| 2013/0077750 | A1 * | 3/2013 | Yabugami | A61B 6/481 378/62 |
| 2013/0079626 | A1 * | 3/2013 | Shmatukha | A61B 6/5205 600/420 |
| 2013/0094744 | A1 * | 4/2013 | Sawada | G06T 5/50 382/132 |
| 2013/0148786 | A1 * | 6/2013 | Kruschel | G06T 5/002 378/62 |
| 2014/0270436 | A1 * | 9/2014 | Dascal | A61B 6/463 382/130 |
| 2014/0307935 | A1 * | 10/2014 | Ishii | G06T 3/0056 382/131 |
| 2015/0150527 | A1 | 6/2015 | Ohishi | |
| 2016/0310095 | A1 * | 10/2016 | Kimoto | G06T 7/62 |

FOREIGN PATENT DOCUMENTS

| | | |
|---|---|---|
| JP | 2003-143479 | 5/2003 |
| JP | 2015-107171 | 6/2015 |

* cited by examiner

MEDICAL IMAGE PROCESSING APPARATUS, X-RAY DIAGNOSIS APPARATUS, AND MEDICAL IMAGE PROCESSING METHOD

CROSS-REFERENCE TO RELATED APPLICATIONS

This application is based upon and claims the benefit of priority from Japanese Patent Application No. 2018-084517, filed on Apr. 25, 2018; the entire contents of which are incorporated herein by reference.

FIELD

Embodiments described herein relate generally to a medical image processing apparatus, an X-ray diagnosis apparatus, and a medical image processing method.

BACKGROUND

Conventionally, an X-ray diagnosis apparatus has a fluoroscopy roadmap function, as a function to support manipulations in intervention treatments. The fluoroscopy roadmap function supports manipulations on a medical device placed in a blood vessel, by generating a blood vessel image while using image data including information about the blood vessel acquired with the use of a contrast agent and further displaying the generated blood vessel image so as to be superimposed on a fluoroscopy image.

In this situation, the fluoroscopy roadmap function is capable of superimposing the blood vessel image on the fluoroscopy image rendering only the medical device, by performing a difference calculating process of calculating the difference from a wire mask image, on the fluoroscopy image on which the blood vessel image is to be superimposed. With this arrangement, the fluoroscopy roadmap function is able to improve efficiency in medical treatments, by clearly displaying the position of the medical device with respect to the blood vessel or the like.

DETAILED DESCRIPTION

A medical image processing apparatus according to an embodiment includes processing circuitry. The processing circuitry is configured to sequentially obtain X-ray images. The processing circuitry is configured to sequentially generate average images by using the obtained plurality of X-ray images, in parallel to the obtainment of the X-ray images. The processing circuitry is configured to sequentially generate difference images by performing a difference calculating process between the X-ray images and the average images, in parallel to the obtainment of the X-ray images and the generation of the average images.

Exemplary embodiments of a medical image processing apparatus, an X-ray diagnosis apparatus, and a medical image processing method will be explained in detail below, with reference to the accompanying drawings. Possible embodiments of the medical image processing apparatus, the X-ray diagnosis apparatus, and the medical image processing method of the present disclosure are not limited to the embodiments described below.

First Embodiment

Figure 1:
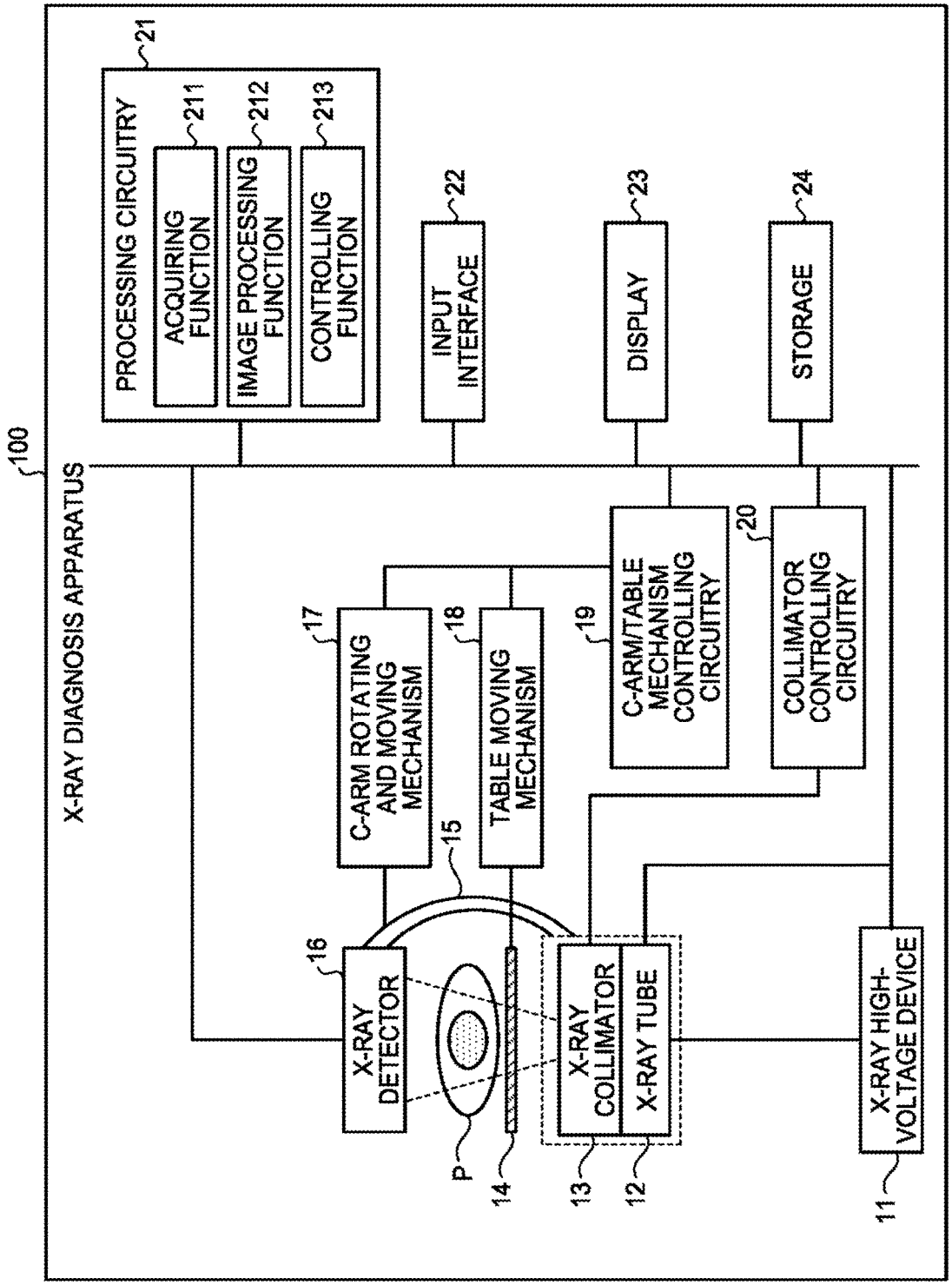
FIG. 1 is a diagram illustrating an exemplary configuration of an X-ray diagnosis apparatus according to a first embodiment.

To begin with, an overall configuration of an X-ray diagnosis apparatus according to a first embodiment will be explained. FIG. 1 is a diagram illustrating an exemplary configuration of an X-ray diagnosis apparatus 100 according to the first embodiment. As illustrated in FIG. 1, the X-ray diagnosis apparatus 100 according to the first embodiment includes an X-ray high-voltage device 11, an X-ray tube 12, an X-ray collimator 13, a table 14, a C-arm 15, an X-ray detector 16, a C-arm rotating and moving mechanism 17, a table moving mechanism 18, C-arm/table mechanism controlling circuitry 19, collimator controlling circuitry 20, processing circuitry 21, an input interface 22, a display 23, and a storage 24.

The X-ray diagnosis apparatus 100 is connected to an injector that is a device configured to inject a contrast agent through a catheter inserted into an examined subject (hereinafter "subject"). The X-ray diagnosis apparatus 100 is configured to transmit and receive electrical signals to and from the injector. In this situation, the contrast agent is injected from the injector according to an injection instruction received via the processing circuitry 21. More specifically, the injector injects the contrast agent, according to an instruction to start injecting the contrast agent and an instruction to stop injecting the contrast agent received from the processing circuitry 21, and also, in accordance with a contrast agent injection condition including an injection speed and the like. The injector is also capable of starting the injection and stopping the injection according to an injection instruction that is directly input to the injector by an operator.

In the X-ray diagnosis apparatus 100 illustrated in FIG. 1, processing functions are stored in the storage 24 in the form of computer-executable programs. The C-arm/table mechanism controlling circuitry 19, the collimator controlling circuitry 20, and the processing circuitry 21 are processors configured to realize the functions corresponding to the programs by reading and executing the programs from the storage 24. In other words, each of the circuits that has read the corresponding program has the function corresponding to the read program.

The X-ray high-voltage device 11 is a high-voltage power source that is configured, under control of the processing circuitry 21, to generate high voltage and to supply the generated high voltage to the X-ray tube 12. The X-ray tube 12 is configured to generate X-rays by using the high voltage supplied thereto from the X-ray high-voltage device 11.

The X-ray collimator 13 is configured, under control of the collimator controlling circuitry 20, to limit the X-rays generated by the X-ray tube 12 so as to be selectively radiated onto a region of interest of a subject P. For example, the X-ray collimator 13 includes four slidable collimator blades. The X-ray collimator 13 is configured, under the control of the collimator controlling circuitry 20, to arbitrarily vary the shape, the size, and the position of an opening, by sliding the collimator blades. As a result of the size and the position of the opening being adjusted by the X-ray collimator 13 in this manner, the size and the position of an X-ray radiation region with respect to a detecting surface of the X-ray detector 16 are adjusted. In other words, the X-rays generated by the X-ray tube 12 are limited by the opening of the X-ray collimator 13 and radiated onto the subject P. In this situation, the collimator blades of the X-ray collimator 13 are slid and moved so that the X-rays are radiated only onto a Region of Interest (ROI) set by the operator, for example. Further, the X-ray collimator 13 may include an additional filter used for adjusting the quality of the X-rays. The additional filter may be configured in accordance with each medical examination to be performed, for example.

The table 14 is a bed on which the subject P is placed and is arranged over a table device (not illustrated). The subject P is not included in the configuration of the X-ray diagnosis apparatus 100.

The X-ray detector 16 is configured to detect X-rays that have passed through the subject P. For example, the X-ray detector 16 includes detecting elements arranged in a matrix formation. The detecting elements are configured to convert the X-rays that have passed through the subject P into electrical signals, to accumulate the electrical signals therein, and to output the accumulated electrical signals to the processing circuitry 21.

The C-arm 15 is configured to hold the X-ray tube 12, the X-ray collimator 13, and the X-ray detector 16. The X-ray tube 12 and the X-ray collimator 13 are positioned by the C-arm 15 so as to oppose the X-ray detector 16, while the subject P is interposed therebetween. Although FIG. 1 illustrates an example in which the X-ray diagnosis apparatus 100 is of a single-plane type, possible embodiments are not limited to this example. The X-ray diagnosis apparatus 100 may be of a bi-plane type. The C-arm 15 is configured to be rotated on each of a plurality of axes individually, by an actuator such as a motor provided for a supporting device.

The C-arm rotating and moving mechanism 17 is a mechanism configured to rotate and move the C-arm by driving the motor or the like provided for the supporting device. The table moving mechanism 18 is a mechanism configured to move the table 14. For example, by using a motive power generated by the actuator, the table moving mechanism 18 is configured to move the table 14.

The C-arm/table mechanism controlling circuitry 19 is configured to adjust the rotating and the moving of the C-arm 15 and the moving of the table 14, by controlling the C-arm rotating and moving mechanism 17 and the table moving mechanism 18, under the control of the processing circuitry 21. The collimator controlling circuitry 20 is configured to control a radiation range of the X-rays radiated onto the subject P, by adjusting the opening degree of the collimator blades included in the X-ray collimator 13 so as to vary the shape, the size, and the position of the opening, under the control of the processing circuitry 21.

The input interface 22 is realized by using a trackball a switch button, a mouse, a keyboard, a touchpad used for performing an input operation by touching an operation surface thereof, a touch screen in which a display screen and a touchpad are integrally formed, a contactless input circuit using an optical sensor, an audio input circuit, and/or the like used for setting a predetermined region (e.g., a ROI) and the like, as well as a foot switch or the like used for radiating the X-rays and the like.

The input interface 22 is connected to the processing circuitry 21 and is configured to convert an input operation received from the operator into an electrical signal and to output the electrical signal to the processing circuitry 21. The input interface 22 of the present disclosure does not necessarily have to include one or more physical operation component parts such as a mouse and a keyboard. For example, possible examples of the input interface include a processing circuit configured to receive an electrical signal corresponding to an input operation from an external input device provided separately from the apparatus and to output the electrical signal to a controlling circuit.

The display 23 is configured to display a Graphical User Interface (GUI) used for receiving instructions from the operator and various types of images generated by the processing circuitry 21. For example, the display 23 is configured to display fluoroscopy roadmap images generated by the processing circuitry 21. Further, the display 23 is configured to display various types of processing results and analysis results obtained by the processing circuitry 21.

The storage 24 is configured to receive and store therein image data generated by the processing circuitry 21. Further, the storage 24 is configured to store therein X-ray images, volume data, contrast-enhanced blood vessel images (angiography images), non-contrast-enhanced blood vessel images (addition mask images), blood vessel sub-mask images, wire mask images, difference images, combined images (fluoroscopy roadmap images), and the like generated by the processing circuitry 21. Details of the images will be explained later.

Further, the storage 24 is configured to store therein programs that correspond to various types of functions and are read and executed by the circuits illustrated in FIG. 1. In one example, the storage 24 stores therein a program corresponding to an acquiring function 211, a program corresponding to an image processing function 212, and a program corresponding to a controlling function 213, each of which is read and executed by the processing circuitry 21. Although the example was explained with reference to FIG. 1 in which the single storage circuit (the storage 24) stores therein the programs corresponding to the processing functions, another arrangement is also acceptable in which a plurality of storage circuits are arranged in a distributed manner so that various circuits including the processing circuitry 21 each read a corresponding program from an individual storage circuit. The storage 24 is an example of storage.

By executing the acquiring function 211, the image processing function 212, and the controlling function 213, the processing circuitry 21 is configured to control operations of the entire X-ray diagnosis apparatus 100. More specifically, by reading and executing the program corresponding to the acquiring function 211 from the storage 24, the processing circuitry 21 executes various types of processes related to acquiring image data. For example, the acquiring function 211 is configured to generate the image data by using the electrical signals converted from the X-rays by the X-ray detector 16 and stores the generated image data into the storage 24. In one example, the acquiring function 211 generates projection data based on the electrical signals, by performing a current/voltage conversion, an analog/digital (A/D) conversion, and a parallel/serial conversion on the electrical signals received from the X-ray detector 16. Further, the acquiring function 211 is configured to store the generated projection data into the storage 24. Further, the acquiring function 211 is also capable of reconstructing reconstruction data (volume data) by using projection data acquired through a rotating imaging process and further storing the reconstructed volume data into the storage 24.

Further, by reading and executing the program corresponding to the image processing function 212 from the storage 24, the processing circuitry 21 executes various types of processes related to image processing processes. For example, the image processing function 212 is configured to control image processing processes and analyzing processes performed on projection data. In one example, the image processing function 212 generates X-ray images by performing various types of image processing processes on the projection data stored in the storage 24. In another example, the image processing function 212 generates X-ray images by obtaining projection data directly from the acquiring function 211 and performing various types of image processing processes on the obtained projection data.

Further, the image processing function 212 is also capable of storing the X-ray images resulting from the image processing processes into the storage 24. For example, the image processing function 212 is capable of performing various types of processes using an image processing filter such as a moving average (smoothing) filter, a Gaussian filter, a median filter, a recursive filter, a band-pass filter, or the like. Further, the image processing function 212 is also capable of generating a three-dimensional image from the volume data. In this regard, the image processing function 212 of the present embodiment is configured to perform an averaging process using a plurality of X-ray images, a subtraction process (a difference calculating process) between X-ray images, a combining process (e.g., a superimposing process) to combine a plurality of X-ray images together, and the like. Details of these processes will be explained later.

Further, by reading and executing the program corresponding to the controlling function 213 configured to control the entire apparatus from the storage 24, the processing circuitry 21 performs various types of processes related to the overall control. For example, the controlling function 213 is configured to control the amount of X-rays to be radiated onto the subject P and turning on and off the X-rays, by controlling the X-ray high-voltage device 11 so as to adjust the voltage supplied to the X-ray tube 12, according to an instruction from the operator that is transferred thereto from the input interface 22. Further, for example, the controlling function 213 is configured to adjust the rotating and the moving of the C-arm 15 and the moving of the table 14, by controlling the C-arm/table mechanism controlling circuitry 19 according to an instruction from the operator.

Further, for example, the controlling function 213 is configured to control the radiation range of the X-rays radiated onto the subject P, by controlling the collimator controlling circuitry 20 and adjusting the opening degree of the collimator blades included in the X-ray collimator 13, according to an instruction from the operator. Further, the controlling function 213 is configured to exercise control so that the display 23 displays a GUI used for receiving instructions from the operator, any of the images stored in the storage 24, processing results obtained by the processing circuitry 21, and the like.

The processing circuitry 21 is an example of processing circuitry.

Figure 2:
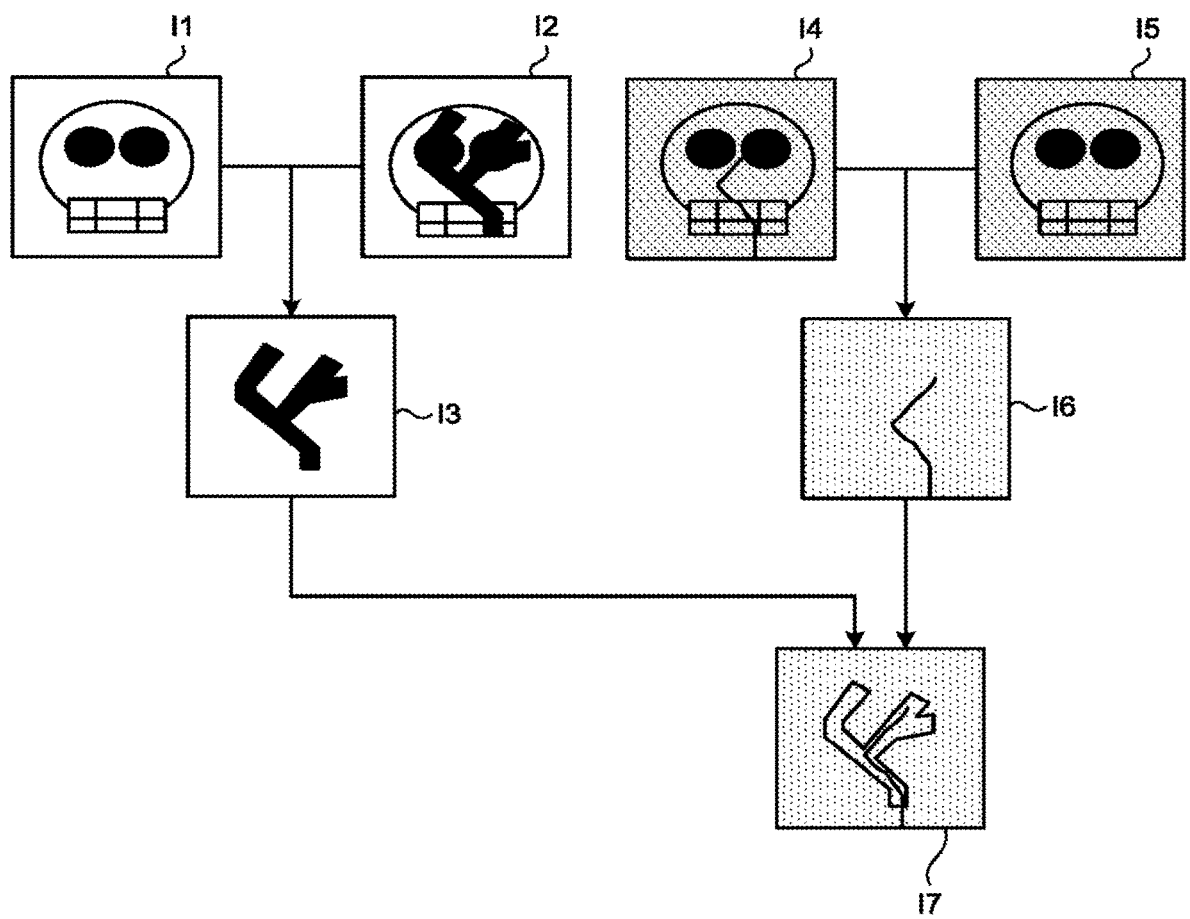
FIG. 2 is a diagram for explaining a fluoroscopy roadmap process according to the first embodiment.

An overall configuration of the X-ray diagnosis apparatus 100 has thus been explained. The X-ray diagnosis apparatus 100 according to the present embodiment structured as described above is configured to improve a sense of operability of a fluoroscopy roadmap function. To begin with, an overview of the fluoroscopy roadmap function will be explained, with reference to FIG. 2. FIG. 2 is a diagram for explaining a fluoroscopy roadmap process according to the first embodiment. The X-ray diagnosis apparatus 100 first acquires blood vessel images by using a contrast agent. For example, the X-ray diagnosis apparatus 100 acquires an X-ray image I1 indicating peripheral tissues (a background) such as bones while no contrast agent is injected in the subject. In this situation, the X-ray diagnosis apparatus 100 is able to acquire the X-ray image I1 in which noise is reduced, by calculating an arithmetic mean of a plurality of X-ray images that are acquired while no contrast agent is injected in the subject.

In that situation, for example, the acquiring function 211 acquires a plurality of pieces of projection data while no contrast agent is injected in the subject. Further, the image processing function 212 generates the X-ray image I1, by generating an X-ray image from each of the acquired plurality of pieces of projection data and calculating an arithmetic mean of the generated plurality of X-ray images. In the following sections, the X-ray image obtained by calculating an arithmetic mean of a plurality of X-ray images acquired while no contrast agent is injected in the subject may also be referred to as an addition mask image.

Further, the image processing function 212 generates an X-ray image I2 including the position and the shape of the blood vessel on the basis of projection data acquired while a contrast agent is injected in the subject. In one example, the acquiring function 211 acquires the projection data based on X-rays that have passed through the subject P into whom the contrast agent has been injected by the injector. Further, the image processing function 212 generates the X-ray image I2 on the basis of the acquired projection data. In the following sections, the X-ray image acquired while a contrast agent is injected in the subject may also be referred to as a contrast-enhanced blood vessel image. Further, the image processing function 212 stores the generated X-ray images I1 and I2 into the storage 24. In this situation, the image processing function 212 may store the generated X-ray images I1 and I2 into the storage 24 after applying a scattered ray correction or a beam hardening correction thereto.

Further, as illustrated in FIG. 2, the image processing function 212 generates a blood vessel image I3 by using the X-ray images I1 and I2. For example, the image processing function 212 generates the blood vessel image I3 emphasizing the blood vessel by removing background elements, by reading the X-ray image I1 and the X-ray image I2 from the storage 24 and calculating the difference between the read X-ray images I1 and I2 and further stores the generated blood vessel image I3 into the storage 24. In this situation, the image processing function 212 is also capable of generating a plurality of blood vessel images by performing a difference calculating process on each of a plurality of contrast-enhanced blood vessel images chronologically acquired while a contrast agent is injected and further storing the generated plurality of blood vessel images into the storage 24.

As the difference calculating processes between the X-ray images, the image processing function 212 is capable of performing either a process of calculating differences between pixel values or a process of calculating the difference after performing a logarithmic transformation on the X-ray images (called a log subtraction process). Further, in the following sections, the blood vessel image emphasizing the blood vessel as a result of the difference calculating process may also be referred to as a blood vessel sub-mask image. Further, the X-ray diagnosis apparatus 100 according to the present embodiment is capable of generating a blood vessel sub-mask image either under a fluoroscopy condition or under an image taking condition having a larger radiation amount than that of the fluoroscopy condition.

Subsequently, the acquiring function 211 sequentially acquires pieces of projection data under the fluoroscopy condition, during a manipulation of an intervention treatment. After that, on the basis of the pieces of projection data sequentially acquired, the image processing function 212 generates a fluoroscopy image 14 and a wire mask image 15 illustrated in FIG. 2. In this situation, the wire mask image is an image used for displaying only the medical device such as a catheter and is generated by calculating an arithmetic mean of a plurality of fluoroscopy images.

Further, as illustrated in FIG. 2, the image processing function 212 generates a difference image I6 obtained by removing the background components other than the medical device, by calculating the difference between the fluoroscopy image 14 and the wire mask image 15. Further, as illustrated in FIG. 2, the image processing function 212 generates a combined image 17 obtained by combining the blood vessel image I3 with the difference image 16. In this situation, the image processing function 212 is also capable of generating the combined image 17, by combining an X-ray image obtained by adjusting (inverting) the pixel values of the blood vessel image I3 so as to make the medical device overlapping with the blood vessel visible, with the difference image I6.

Every time a fluoroscopy image 14 is generated, the image processing function 212 performs a difference calculating process thereon with the wire mask image 15 so as to sequentially generate difference images 16. The image processing function 212 thus sequentially generates combined images 17 by using the generated difference images. By sequentially displaying the combined images 17 generated in this manner, the fluoroscopy roadmap function is able to display images that clearly indicate the manipulation on the medical device applied to the blood vessel.

Figure 3:
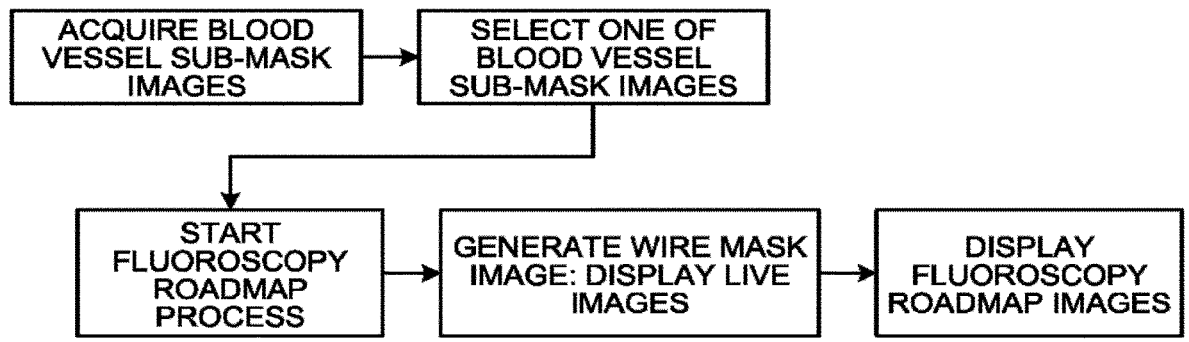
FIG. 3 is a diagram for explaining a commonly-used procedure in a fluoroscopy roadmap process.

In this situation, as explained above, during the fluoroscopy roadmap process, the wire mask image would be generated by using the fluoroscopy images acquired after the intervention treatment is started. In other words, as illustrated in FIG. 3, to perform the fluoroscopy roadmap process, the blood vessel sub-mask images would be acquired, and one of the blood vessel sub-mask images used for the fluoroscopy roadmap process would be selected, and subsequently, the fluoroscopy roadmap process would be started when a fluoroscopy button is pressed. In the fluoroscopy roadmap process, the wire mask image would subsequently be generated, and the fluoroscopy roadmap images would be displayed. In this manner, during the fluoroscopy roadmap process, lying between the time when the user presses the fluoroscopy switch to start the fluoroscopy process and the time when the fluoroscopy roadmap images are displayed would be the time period required by the generation of the wire mask image. During that period of time, for example, a plurality of fluoroscopy images (live images) acquired for generating the wire mask image would be displayed on the displayed device.

Accordingly, for the user who presses the fluoroscopy button while expecting the fluoroscopy roadmap images to be displayed, the display of the fluoroscopy images before the wire mask image is generated would be unexpected and would be difficult to understand. Further, the wire mask image would be generated in approximately one or two seconds after the fluoroscopy button is pressed, and the display would be switched from the live images to the fluoroscopy roadmap images. Thus, the user might find the display cumbersome and might feel that the sense of operability is unsatisfactory.

Figure 4:
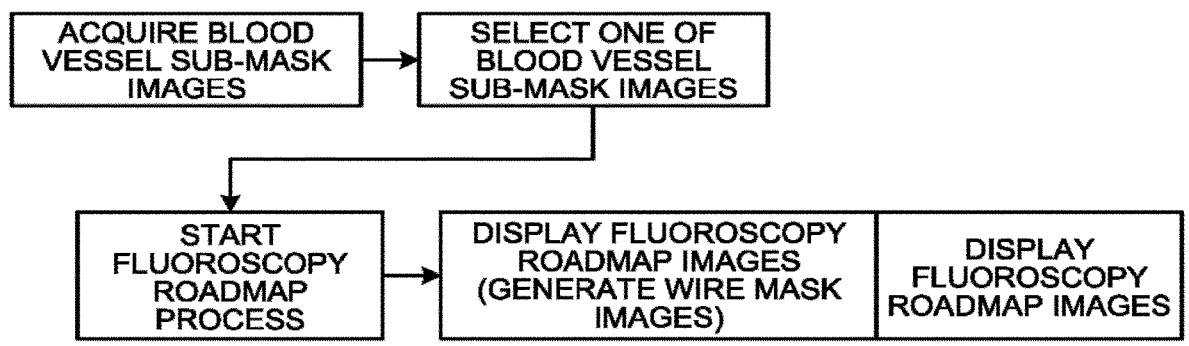
FIG. 4 is a diagram for explaining a procedure in a fluoroscopy roadmap process performed by the X-ray diagnosis apparatus according to the first embodiment.

To cope with this situation, as illustrated in FIG. 4, the X-ray diagnosis apparatus 100 according to the first embodiment improves the sense of operability of the fluoroscopy roadmap function, by exercising control so as to have fluoroscopy roadmap images displayed immediately after the fluoroscopy button is pressed to start the fluoroscopy roadmap process. In other words, the X-ray diagnosis apparatus 100 according to the first embodiment causes the fluoroscopy roadmap images to be displayed immediately after the fluoroscopy button is pressed, by arranging the fluoroscopy roadmap images to be displayed while generating the wire mask image. Further, as illustrated in FIG. 4, after the wire mask image is generated, the X-ray diagnosis apparatus 100 according to the first embodiment exercises control so as to keep the fluoroscopy roadmap images while using the generated wire mask image. Details of the control will be explained below. FIG. 3 is a diagram for explaining the commonly-used procedure in the fluoroscopy roadmap process. Further, FIG. 4 is a diagram for explaining the procedure in the fluoroscopy roadmap process performed by the X-ray diagnosis apparatus 100 according to the first embodiment.

Figure 5:
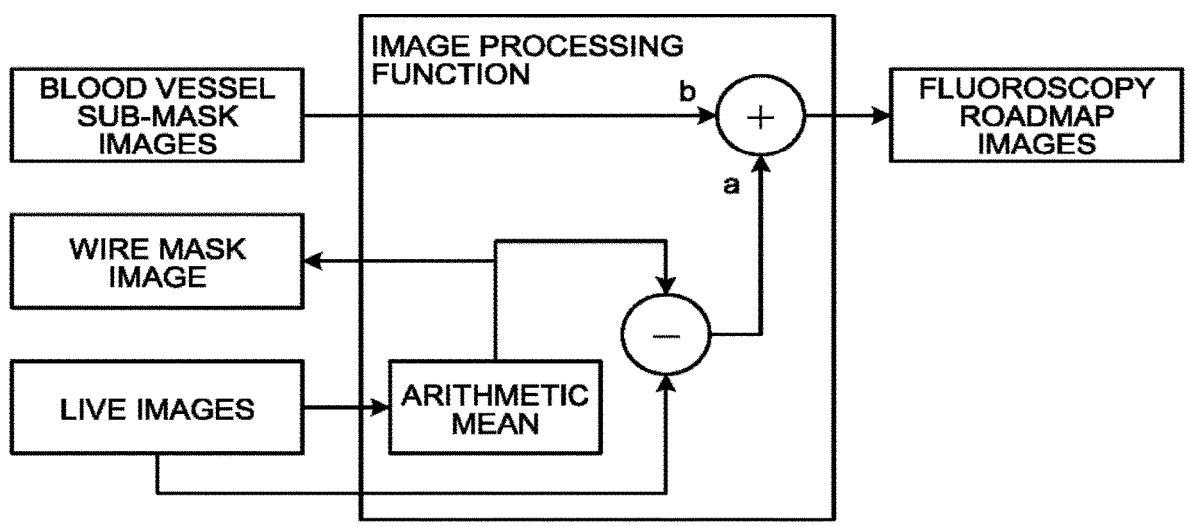
FIG. 5 is a diagram for explaining a process performed by an image processing function according to the first embodiment.

FIG. 5 is a diagram for explaining a process performed by the image processing function 212 according to the first embodiment. In this situation, FIG. 5 illustrates the process performed by the image processing function 212 after the blood vessel sub-mask image is generated. In other words, the following sections will describe the process performed by the image processing function 212 after the blood vessel sub-mask image is generated by acquiring an addition mask image and contrast-enhanced blood vessel images and is stored into the storage 24.

In parallel to the obtainment of the X-ray images, the image processing function 212 sequentially generates wire mask images by using the obtained plurality of X-ray images. Further, the image processing function 212 sequentially generates difference images by performing a difference calculating process on the obtained X-ray images and the generated mask images. For example, as illustrated in FIG. 5, the image processing function 212 generates a wire mask image by calculating an arithmetic mean of the sequentially-acquired live images and further generates the difference images by calculating differences between the live images of which the arithmetic mean is calculated and the generated wire mask image.

In this situation, the live images are intermittently acquired in accordance with a set framerate, while the user is pressing the fluoroscopy switch included in the input interface 22. Every time a live image is acquired, the image processing function 212 generates a wire mask image by using a plurality of live images that have already been acquired and, when the condition is satisfied where the quantity of the live images used for generating a wire mask image has reached a predetermined value, the image processing function 212 stops generating wire mask images and further stores the wire mask image generated by using the live images of which the quantity is equal to the predetermined value, into the storage 24.

For example, every time a live image is acquired, the image processing function 212 calculates an arithmetic mean until the quantity of the live images reaches a value "n" that is designated in advance and stores the result of the arithmetic mean calculation that has so far been performed, into the storage 24, as a wire mask image. In other words, the wire mask image stored in the storage 24 is updated at every frame for the time period corresponding to "n" frames from the start. Further, for the (n+1)-th frame and thereafter, the image processing function 212 uses the wire mask image resulting from the arithmetic mean calculation up to the n-th frame for the difference calculating process, without calculating an arithmetic mean. In this situation, the quantity "n" of the live images used for generating the wire mask image may be set in advance or may be set by the user via the input interface.

Figure 6:
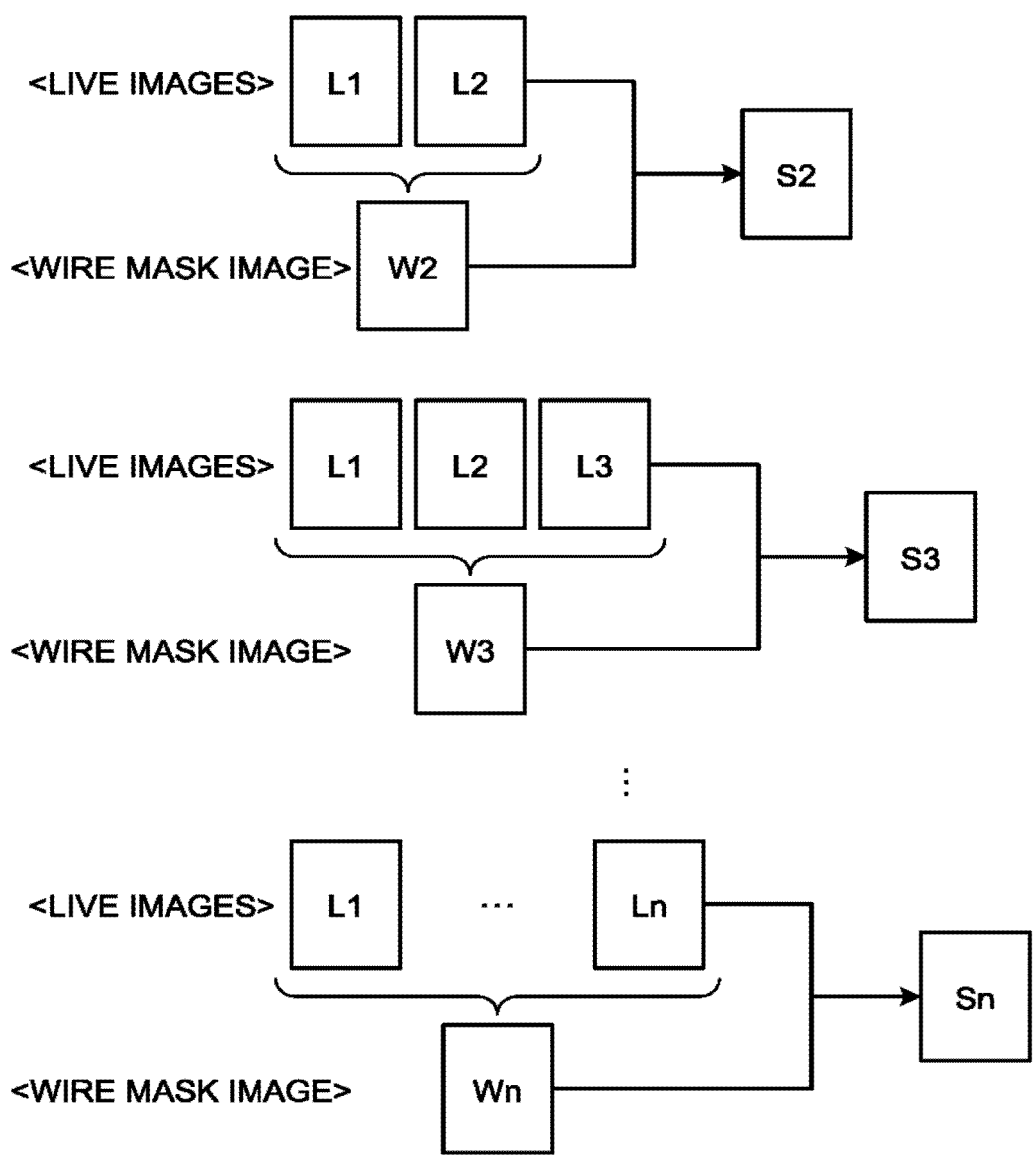
FIG. 6 is a diagram for explaining an example of a difference calculating process performed by the image processing function according to the first embodiment.

Further, the image processing function 212 generates difference images in parallel to the generation of the wire mask images described above. More specifically, every time a live image is acquired, the image processing function 212 generates a difference image by performing a difference calculating process with the generated wire mask image (or the wire mask image already stored in the storage 24). FIG. 6 is a diagram for explaining an example of the difference calculating process performed by the image processing function 212 according to the first embodiment. In this situation, FIG. 6 illustrates a process up to the n-th live image. In this situation, when the frame that is the first to be acquired after the fluoroscopy process is started is stored as a wire mask image, because the difference calculating process is performed between the two first frames, all of the image information in the difference image will be eliminated.

For example, when the second frame since the start of the fluoroscopy process is acquired, the image processing function 212 generates, as illustrated in the top section of FIG. 6, a wire mask image W2 by calculating an arithmetic mean of a live image L1 in the first frame and a live image L2 in the second frame. After that, the image processing function 212 generates a difference image S2 by calculating the difference between the generated wire mask image W2 and the live image L2. In this situation, the image processing function 212 updates the wire mask image stored in the storage 24 with the wire mask image W2.

Similarly, when the third frame since the start of the fluoroscopy process is acquired, the image processing function 212 generates, as illustrated in the middle section of FIG. 6, a wire mask image W3 by calculating an arithmetic mean of the live image L1, the live image L2, and a live image L3 in the third frame. After that, the image processing function 212 generates a difference image S3 by calculating the difference between the generated wire mask image W3 and the live image L3. In this situation, the image processing function 212 updates the wire mask image stored in the storage 24 with the wire mask image W3.

The image processing function 212 sequentially performs the process described above up to the n-th frame. In other words, when the n-th frame since the start of the fluoroscopy process is acquired, the image processing function 212 generates, as illustrated in the bottom section of FIG. 6, a wire mask image Wn by calculating an arithmetic mean of the live images from the live image L1 up to the live image Ln in the n-th frame. After that, the image processing function 212 generates a difference image Sn, by calculating the difference between the generated wire mask image Wn and the live image Ln. In this situation, the image processing function 212 updates the wire mask image stored in the storage 24 with the wire mask image Wn. For the (n+1)-th frame and thereafter, the image processing function 212 generates difference images by calculating the differences between the wire mask image Wn stored in the storage 24 and the live images.

Subsequently, every time a difference image is generated, the image processing function 212 generates a fluoroscopy roadmap image obtained by combining the difference image with a blood vessel sub-mask image. In this situation, for example, as illustrated in FIG. 5, the image processing function 212 combines the difference image multiplied by an arbitrary coefficient "a" with the blood vessel sub-mask image multiplied by an arbitrary coefficient "b". As a result, the controlling function 213 is able to cause the display 23 to display fluoroscopy roadmap images in which the density of the blood vessel and the density of the medical device are adjusted. For example, from the start of the fluoroscopy process up to the n-th frame, the wire mask images are successively updated by using the live images. Accordingly, a picture of the medical device such as a guide wire that is held and manipulated by the user in the X-ray radiation field during that period of time is contained in the wire mask images after going through the arithmetic mean calculation. As a result, with respect to such pixels in which a picture of the medical device in a live image overlaps with the picture of the medical device in the wire mask image, the difference is calculated between the pictures of the medical device. Thus, there is a possibility that visibility of the medical device in the fluoroscopy roadmap images may be degraded. To cope with this situation, by increasing the arbitrary coefficient "a" by which each of the difference images is multiplied, the image processing function 212 is able to improve the visibility of the medical device.

Further, every time a difference image is combined with the blood vessel sub-mask image, the controlling function 213 exercises control so that the display 23 displays a combined fluoroscopy roadmap image. For example, the controlling function 213 causes the display 23 to display a fluoroscopy roadmap image obtained by combining the difference image S2 with the blood vessel sub-mask image and to subsequently display another fluoroscopy roadmap image obtained by combining the difference image S3 with the blood vessel sub-mask image. In this manner, as the live images are acquired, the controlling function 213 causes the display 23 to sequentially display the fluoroscopy roadmap images that are generated on the basis of the acquired live images.

When the user releases the fluoroscopy switch, the emission of the X-rays is stopped. In this situation, the controlling function 213 may exercise control so that the last fluoroscopy roadmap image keeps being displayed. Further, when the fluoroscopy switch is pressed again by the user, because the wire mask image has already been generated and stored in the storage 24, the image processing function 212 reads the wire mask image stored in the storage 24 and generates difference images by performing a difference calculating process between the read wire mask image and the acquired live images.

Figure 7:
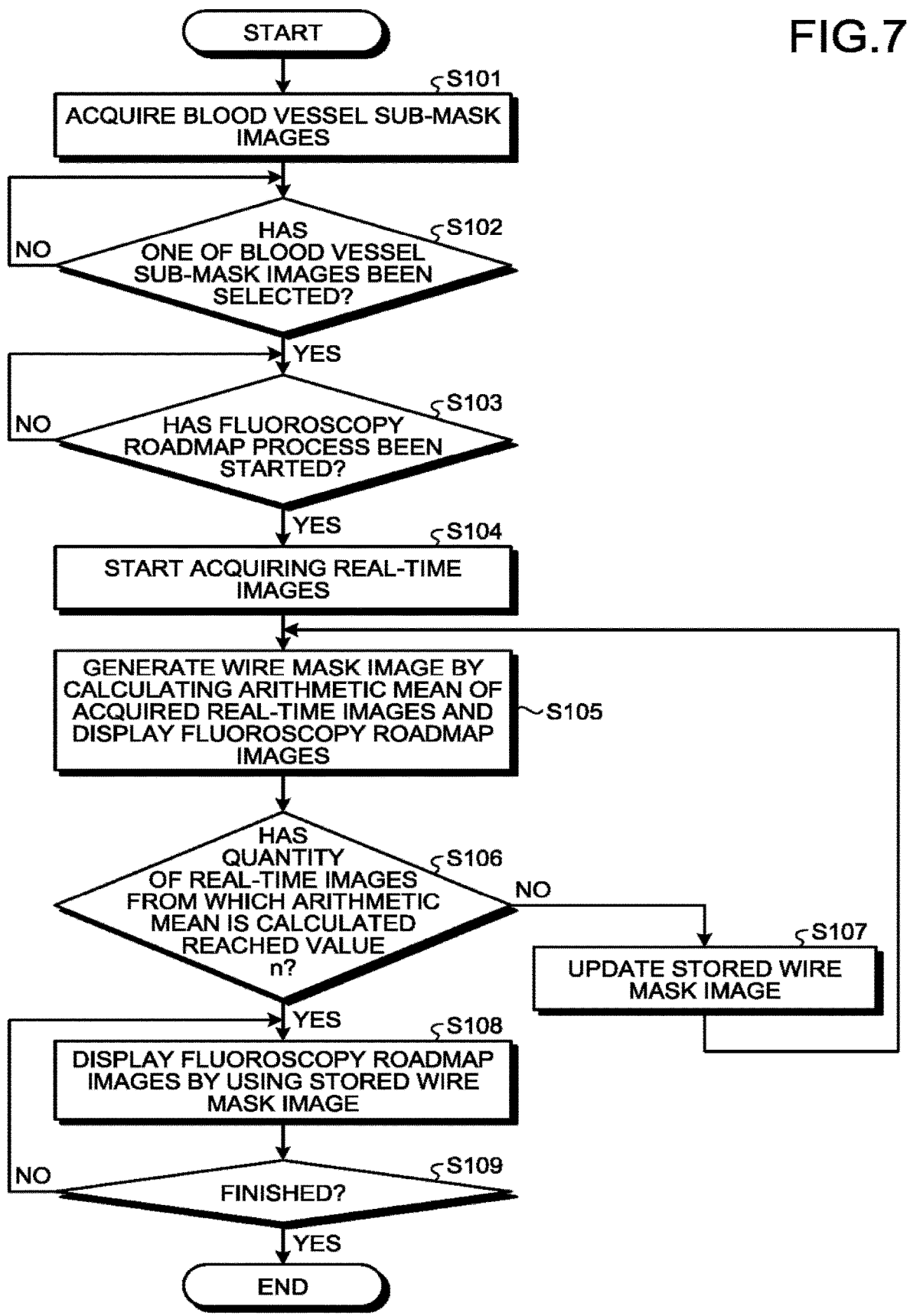
FIG. 7 is a flowchart illustrating a processing procedure performed by the X-ray diagnosis apparatus according to the first embodiment.

Next, a process performed by the X-ray diagnosis apparatus 100 according to the first embodiment will be explained, with reference to FIG. 7. FIG. 7 is a flowchart illustrating a processing procedure performed by the X-ray diagnosis apparatus 100 according to the first embodiment. Steps S101 and S104 through S108 illustrated in FIG. 7 are steps at which the processing circuitry 21 reads and executes the programs corresponding to the acquiring function 211, the image processing function 212, and the controlling function 213 from the storage 24. Steps S102, S103, and S109 are steps at which the processing circuitry 21 reads and executes the program corresponding to the controlling function 213 from the storage 24.

For example, as illustrated in FIG. 7, the processing circuitry 21 acquires blood vessel sub-mask images according to an instruction received from the user via the input interface 22 (step S101) and judges whether or not a blood vessel sub-mask image to be used for a fluoroscopy roadmap process has been selected from among the acquired blood vessel sub-mask images (step S102). In this situation, when one of the blood vessel sub-mask images has been selected (step S102: Yes), the processing circuitry 21 judges whether or not a fluoroscopy button has been pressed to start the fluoroscopy roadmap process (step S103). On the contrary, until it is determined at step S102 that one of the blood vessel sub-mask images has been selected (step S102: No), the processing circuitry is in a standby state.

When it is determined at step S103 that the fluoroscopy roadmap process is started (step S103: Yes), the processing circuitry 21 starts acquiring real-time images (step S104), generates a wire mask image by calculating an arithmetic mean of the acquired real-time images, and causes the display 23 to display fluoroscopy roadmap images (step S105). On the contrary, until it is determined at step S103 that the fluoroscopy roadmap process is started (step S103: No), the processing circuitry is in a standby state.

Subsequent to step S105, the processing circuitry 21 judges whether or not the quantity of the real-time images from which the arithmetic mean is calculated has reached the predetermined value "n" (step S106). When the quantity has not reached the value "n", the processing circuitry 21 updates the stored wire mask image (step S107) and returns to step S105 where the processing circuitry 21 generates a wire mask image by using the newly-generated real-time image, generates difference images by using the generated wire mask image, and further causes fluoroscopy roadmap images to be displayed.

On the contrary, when it is determined at step S106 that the quantity has reached the value "n", the processing circuitry 21 updates the wire mask image stored in the storage 24 with the wire mask image generated by using the "n" real-time images, also generates difference images by using the stored wire mask image, and further causes fluoroscopy roadmap images to be displayed (step S108).

After that, the processing circuitry 21 judges whether or not the fluoroscopy roadmap process is finished (step S109). When the fluoroscopy roadmap process is not finished (step S109: No), the processing circuitry 21 generates difference images by using the newly-generated real-time image and the stored wire mask image and further causes fluoroscopy roadmap images to be displayed. In this situation, until it is determined at step S109 that the fluoroscopy roadmap process is finished, the fluoroscopy roadmap process using the stored wire mask image is continued.

As explained above, according to the first embodiment, the acquiring function 211 is configured to sequentially obtain the live images. In parallel to the acquisition of the live images, the image processing function 212 is configured to sequentially generate the wire mask images by using the acquired plurality of live images. The image processing function 212 is configured to sequentially generate the difference images by performing the difference calculating process between the acquired live images and the generated wire mask images. Consequently, the X-ray diagnosis apparatus 100 according to the first embodiment is able to exercise control so as to display the fluoroscopy roadmap images immediately after the fluoroscopy button is pressed to start the fluoroscopy roadmap process. Accordingly, the X-ray diagnosis apparatus 100 according to the first embodiment makes it possible to improve the sense of operability of the fluoroscopy roadmap function.

Further, according to the first embodiment, the image processing function 212 is configured to sequentially generate the fluoroscopy roadmap images by combining the difference images with the blood vessel sub-mask image that is substantially in the same position as the live images. The controlling function 213 is configured to exercise control so as to sequentially display the fluoroscopy roadmap images. Consequently, the X-ray diagnosis apparatus 100 according to the first embodiment is able to display the fluoroscopy roadmap images immediately after the fluoroscopy button is pressed to start the fluoroscopy roadmap process. Thus, the X-ray diagnosis apparatus 100 according to the first embodiment is able to behave more suitable for intuitions of the user.

Further, according to the first embodiment, the image processing function 212 is configured, every time a live image is obtained, to generate the wire mask image by using the already-obtained plurality of live images. When the condition is satisfied where the quantity of the live images used for generating the wire mask image has reached the predetermined value, the image processing function 212 is configured to stop generating the wire mask images and to store the wire mask image generated by using the wire mask images of which the quantity is equal to the predetermined value, into the storage 24. With respect to the live images obtained while exceeding the predetermined value, the image processing function 212 is configured to perform the difference calculating process by using the wire mask image stored in the storage 24. Consequently, the X-ray diagnosis apparatus 100 according to the first embodiment is able to generate the wire mask images in which the noise is reduced, in parallel to the display of the fluoroscopy roadmap images. Thus, the X-ray diagnosis apparatus 100 according to the first embodiment makes it possible to improve the sense of operability of the fluoroscopy roadmap function.

Second Embodiment

In the first embodiment described above, the example is explained in which the wire mask image is generated by using the live images of which the quantity is equal to "n" as counted from the first live image since the start of the fluoroscopy roadmap process. In a second embodiment, an example will be explained in which live images in a certain quantity as counted from the first live image since the start of the fluoroscopy roadmap process are eliminated from an eventual wire mask image. In the following sections, some of the constituent elements that are the same as those in the first embodiment will be referred to by using the same reference characters, and the explanations thereof may be omitted.

The image processing function 212 according to the second embodiment is configured, every time a live image is obtained, to generate a wire mask image by using the already-obtained live images. When the condition is satisfied where the quantity of the obtained live images has reached a first predetermined value, the image processing function 212 is configured to stop generating the wire mask images and to store, into the storage 24, a wire mask image generated by using live images that are among the live images of which the quantity is equal to the first predetermined value and of which the quantity is equal to a second predetermined value as counted from the most recent live image. Further, the image processing function 212 is configured to perform a difference calculating process on the live images obtained while exceeding the first predetermined value, by using the live images stored in the storage 24.

Figure 8:
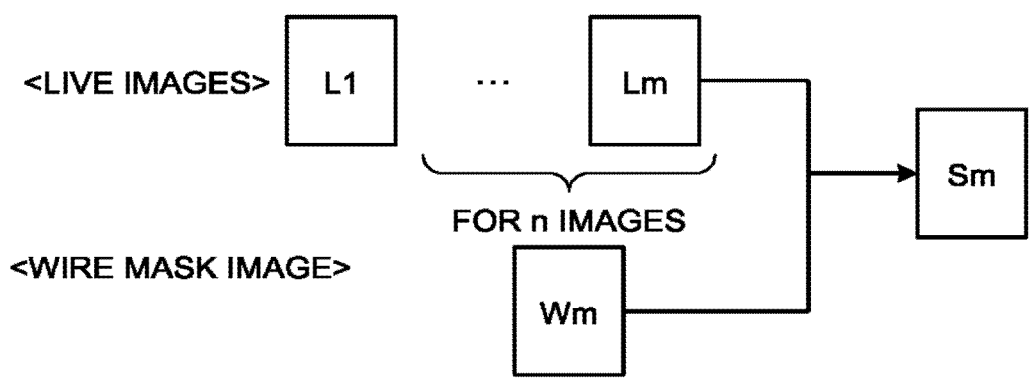
FIG. 8 is a diagram for explaining a wire mask image generating process performed by an image processing function according to a second embodiment.

FIG. 8 is a diagram for explaining a wire mask image generating process performed by the image processing function 212 according to the second embodiment. For example, when a fluoroscopy roadmap process is started, the image processing function 212 according to the second embodiment displays fluoroscopy roadmap images while generating wire mask images, similarly to the first embodiment. Further, as illustrated in FIG. 8, the image processing function 212 according to the second embodiment calculates an arithmetic mean of the live images from the first live image L1 since the fluoroscopy roadmap process is started up to the m-th live image Lm (where m>n) that are used for generating a wire mask image.

In this situation, when the live images of which the quantity is equal to or larger than "n" have been acquired, the image processing function 212 generates a wire mask image by using "n" frames counted from the most recent frame. In other words, when the m-th live image Lm is acquired, the image processing function 212 generates a wire mask image Wm by calculating an arithmetic mean of the "n" live images counted from the live image Lm, as illustrated in FIG. 8. In other words, as the wire mask image to eventually be stored, the image processing function 212 generates the wire mask image while eliminating the first "M−n" frames from the live images L1 to Lm.

In one example, by setting m to satisfy "m=n+10", the image processing function 212 is able to generate a wire mask image while eliminating the first 10 frames. To keep the brightness values of the X-ray images constant, the X-ray diagnosis apparatus 100 has an Automatic Brightness Control (ABC) function that automatically adjusts the amount of X-rays. When a fluoroscopy process is started, the X-ray diagnosis apparatus 100 may have a fluctuation in pixel values among the first frames due to the ABC function. The X-ray diagnosis apparatus 100 according to the second embodiment is able to generate and store the wire mask image while eliminating the X-ray images having such a fluctuation and is therefore able to display fluoroscopy roadmap images that are easier to observe.

Figure 9:
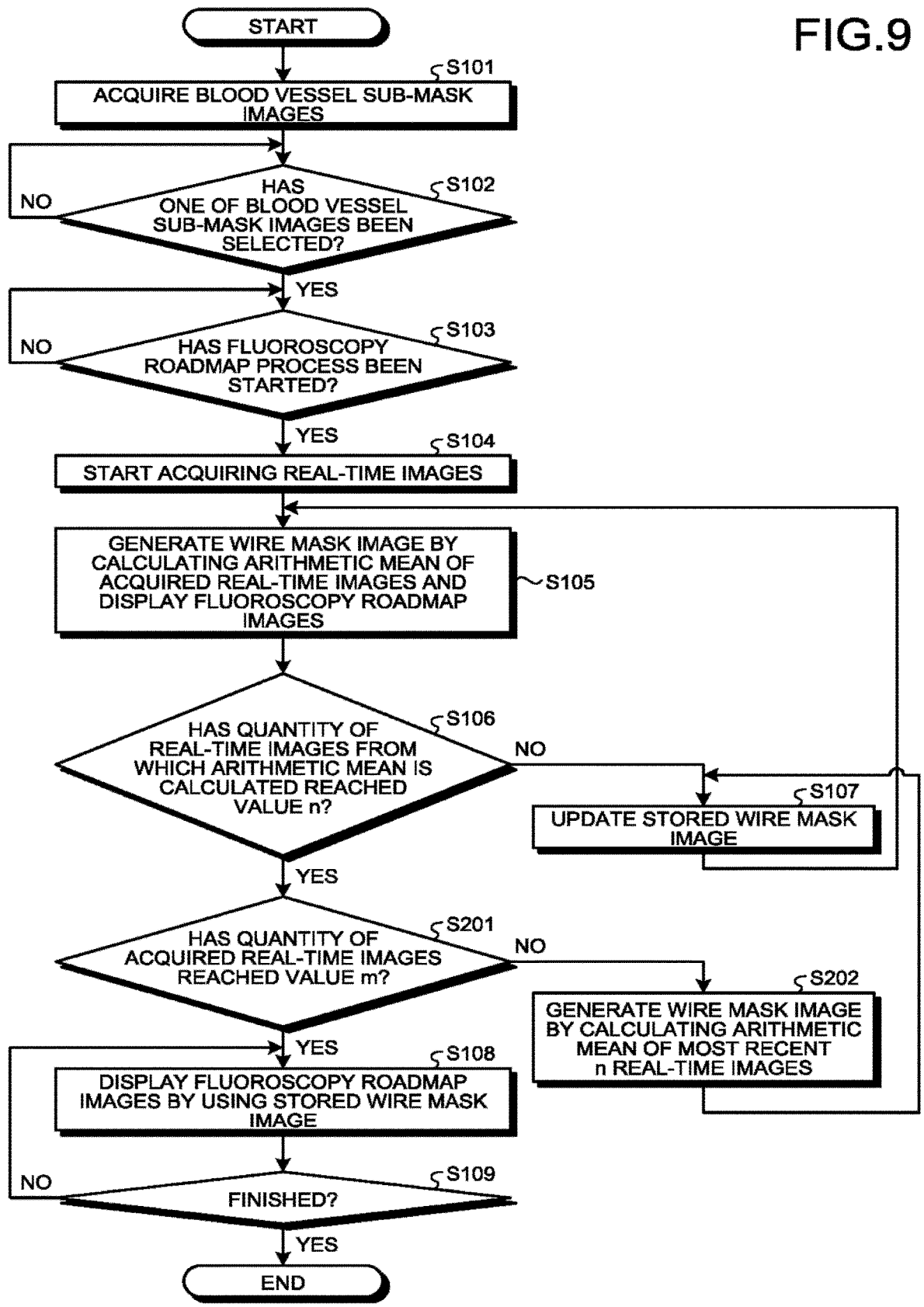
FIG. 9 is a flowchart illustrating a processing procedure performed by an X-ray diagnosis apparatus according to the second embodiment.

Next, a process performed by the X-ray diagnosis apparatus 100 according to the second embodiment will be explained, with reference to FIG. 9. FIG. 9 is a flowchart illustrating a processing procedure performed by the X-ray diagnosis apparatus 100 according to the second embodiment. In FIG. 9, some of the processes that are the same as those in the first embodiment (in FIG. 7) are referred to by using the same reference characters. Steps S201 and S202 in FIG. 9 are steps at which the processing circuitry 21 reads and executes the program corresponding to the image processing function 212 from the storage 24.

For example, as illustrated in FIG. 9, the processing circuitry 21 acquires blood vessel sub-mask images according to an instruction received from the user via the input interface 22 (step S101) and judges whether or not a blood vessel sub-mask image to be used for a fluoroscopy roadmap process has been selected from among the acquired blood vessel sub-mask images (step S102). In this situation, when one of the blood vessel sub-mask images has been selected (step S102: Yes), the processing circuitry 21 judges whether or not a fluoroscopy button has been pressed to start the fluoroscopy roadmap process (step S103). On the contrary, until it is determined at step S102 that one of the blood vessel sub-mask images has been selected (step S102: No), the processing circuitry is in a standby state.

When it is determined at step S103 that the fluoroscopy roadmap process is started (step S103: Yes), the processing circuitry 21 starts acquiring real-time images (step S104), generates a wire mask image by calculating an arithmetic mean of the acquired real-time images, and causes the display 23 to display fluoroscopy roadmap images (step S105). On the contrary, until it is determined at step S103 that the fluoroscopy roadmap process is started (step S103: No), the processing circuitry is in a standby state.

Subsequent to step S105, the processing circuitry 21 judges whether or not the quantity of the real-time images from which the arithmetic mean is calculated has reached the predetermined value "n" (step S106). When the quantity has not reached the value "n", the processing circuitry 21 updates the stored wire mask image (step S107) and returns to step S105 where the processing circuitry 21 generates a wire mask image by using the newly-generated real-time image, generates difference images by using the generated wire mask image, and further causes fluoroscopy roadmap images to be displayed.

On the contrary, when it is determined at step S106 that the quantity has reached the value "n", the processing circuitry 21 judges whether or not the quantity of the acquired real-time images has reached the value "m" (step S201). When the quantity of the acquired real-time images has not reached the value "m" (step S201: No), the processing circuitry 21 generates a wire mask image by calculating an arithmetic mean of the most recent "n" real-time images (step S202) and updates the stored wire mask image therewith (step S107).

On the contrary, when it is determined at step S201 that the quantity of the acquired real-time images has reached the value "m" (step S201: No), the processing circuitry 21 updates the wire mask image stored in the storage 24 with a wire mask image generated by using the "n" real-time images counted from the m-th real-time image, generates difference images by using the stored wire mask image, and further causes fluoroscopy roadmap images to be displayed (step S108).

After that, the processing circuitry 21 judges whether or not the fluoroscopy roadmap process is finished (step S109). When the fluoroscopy roadmap process is not finished (step S109: No), the processing circuitry 21 generates difference images by using the newly-generated real-time image and the stored wire mask image and further causes fluoroscopy roadmap images to be displayed. In this situation, until it is determined at step S109 that the fluoroscopy roadmap process is finished, the fluoroscopy roadmap process using the stored wire mask image is continued.

As explained above, according to the second embodiment, every time a live image is obtained, the image processing function 212 is configured to generate a wire mask image by using the already-obtained plurality of live images. When the condition is satisfied where the quantity of the obtained live images has reached the first predetermined value (i.e., m), the image processing function 212 is configured to stop generating the live images and to store, into the storage 24, the wire mask image generated by using the live images that are among the live images of which the quantity is equal to the first predetermined value and of which the quantity is equal to the second predetermined value (i.e., n) counted from the most recent live image. Further, the image processing function 212 is configured to perform the difference calculating process on the live images obtained while exceeding the first predetermined value, by using the wire mask image stored in the storage 24. Consequently, the X-ray diagnosis apparatus 100 according to the second embodiment makes it possible to display the fluoroscopy roadmap images that are easier to observe.

Third Embodiment

In the first and the second embodiments described above, the example was explained in which the live images are acquired at a constant framerate during the fluoroscopy roadmap process. In a third embodiment, an example will be explained in which the framerate is increased for the time period during which the wire mask images are generated. In the following sections, some of the constituent elements that are the same as those in the first embodiment will be referred to by using the same reference characters, and the explanations thereof may be omitted.

The controlling function 213 according to the second embodiment is configured to exercise control so that, for the time period during which the wire mask images are generated, the framerate used for acquiring the live images is relatively higher. For example, the controlling function 213 controls the X-ray high-voltage device 11 and the X-ray detector 16 so that, for the time period corresponding to either n frames or m frames since the start of the fluoroscopy roadmap process, the framerate is increased within the range of a rated value of the apparatus or a legal restriction, while maintaining the condition of X-rays per emission.

In this situation, the rated value of the apparatus is defined by, for example, a rated output of the X-ray tube 12 or the time it takes to read an image from the X-ray detector 16. Further, the legal restriction may be, for example, the amount of radiation entering the subject per unit time period. For example, when it takes "10 ms" to read an image from the X-ray detector 16, during a fluoroscopy process having a pulse width of "20 ms" per frame at the rate of 15 frames per second, it takes approximately "30 ms" per frame to execute both the radiation of the X-rays and the reading of the image. Accordingly, when the framerate is increased while keeping the same X-ray condition ("30 ms" per frame), it is possible to increase the framerate up to approximately 30 frames per second because 1000 ms/30 ms=33.3 frames.

Further, the rated value of the X-ray tube 12 may be determined by referring to, for example, a Look-Up Table (LUT) indicating an upper limit value of the product of an X-ray tube current value, a pulse width, and a framerate corresponding to each of various X-ray tube voltage levels. The legal restriction may be determined, for example, by estimating the amount of radiation entering the subject on the basis of the product of an X-ray tube voltage level, an X-ray tube current value, a pulse width, and a framerate and further comparing the estimated radiation amount with a legal defined value. Accordingly, the controlling function 213 may exercise control so as to maximize the framerate during the time period corresponding to either n frames or m frames, while using "1/{[pulse width]+[reading time period]}" (frames per second) as a physical upper limit, and taking the rated value of the apparatus and the legal restriction into account.

Figure 10:
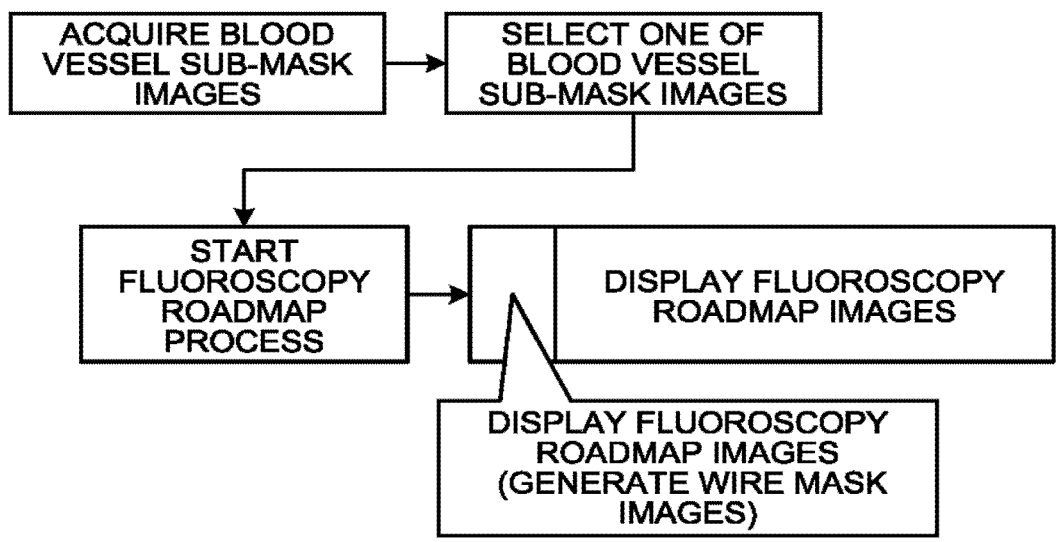
FIG. 10 is a diagram for explaining control exercised by a controlling function according to a third embodiment.

FIG. 10 is a diagram for explaining the control exercised by the controlling function 213 according to the third embodiment. As explained above, the controlling function 213 according to the third embodiment is configured to exercise control so as to increase the framerate for the time period during which the wire mask images are generated. Consequently, as illustrated in FIG. 10, the controlling function 213 is able to shorten the time period required by the generation of the wire mask images, compared to that in the first and the second embodiments. For example, when a medical device is manipulated in the time period during which the wire mask images are generated, the difference images will be impacted because the medical device is rendered in the wire mask images. Accordingly, it is desirable to keep the time period required by the generation of the wire mask images as short as possible. The X-ray diagnosis apparatus 100 according to the third embodiment is able to shorten the time period required by the generation of the wire mask images and is therefore able to reduce the impacts that may be caused by the medical device being moved around during that time period.

Fourth Embodiment

In the first to the third embodiments described above, the example is explained in which the wire mask images are each generated by using the live images acquired after the fluoroscopy roadmap process is started. In a fourth embodiment, another example will be explained in which the addition mask image used at the time of generating the blood sub-mask images is used as a wire mask image. In the following sections, some of the constituent elements that are the same as those in the first embodiment will be referred to by using the same reference characters, and the explanations thereof may be omitted.

Figure 11:
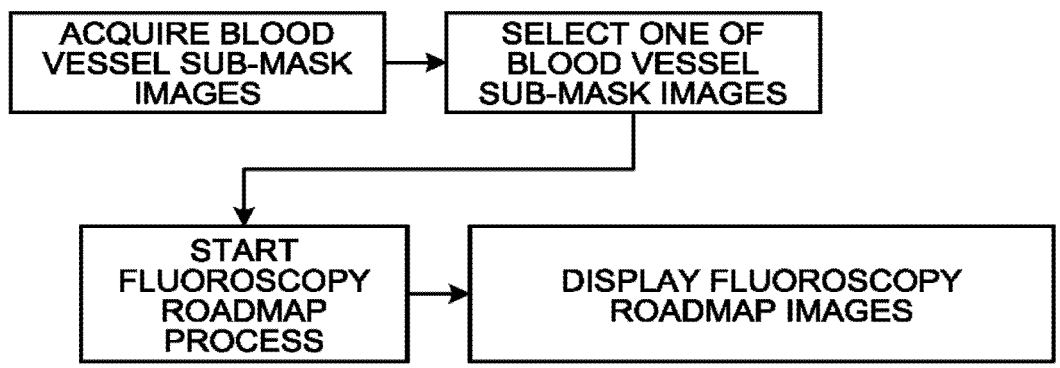
FIG. 11 is a diagram for explaining a procedure in a fluoroscopy roadmap process performed by an X-ray diagnosis apparatus according to a fourth embodiment.

As mentioned above, the image processing function 212 according to the fourth embodiment is configured to use the addition mask image as a wire mask image. In that situation, as illustrated in FIG. 11, it is possible to display fluoroscopy roadmap images without having to generate the wire mask image after the fluoroscopy roadmap process is started. It is therefore possible to improve the sense of operability of the fluoroscopy roadmap function. FIG. 11 is a diagram for explaining a procedure in the fluoroscopy roadmap process performed by the X-ray diagnosis apparatus 100 according to the fourth embodiment.

Figure 12:
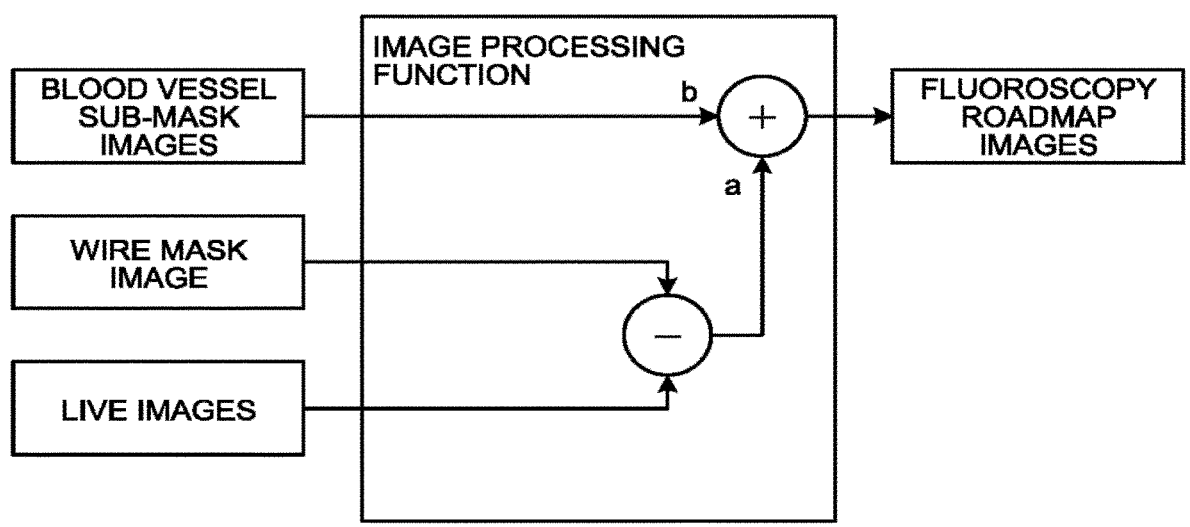
FIG. 12 is a diagram for explaining a process performed by an image processing function according to the fourth embodiment.

FIG. 12 is a diagram for explaining a process performed by the image processing function 212 according to the fourth embodiment. FIG. 12 illustrates the process performed by the image processing function 212 after blood vessel sub-mask images are generated. In other words, the following sections will describe the process performed by the image processing function 212 after the blood vessel sub-mask images are generated by acquiring the addition mask image and the contrast-enhanced blood vessel images and is stored into the storage 24.

As illustrated in FIG. 12, the image processing function 212 according to the fourth embodiment is configured to generate difference images by calculating the differences between the sequentially-acquired live images and the wire mask image stored in the storage 24. After that, every time a difference image is generated, the image processing function 212 is configured to generate a fluoroscopy roadmap image by combining the difference image with the blood vessel sub-mask image. In this situation, for example, as illustrated in FIG. 12, the image processing function 212 combines the difference image multiplied by the arbitrary coefficient "a" with the blood vessel sub-mask image multiplied by the arbitrary coefficient "b".

Figure 13:
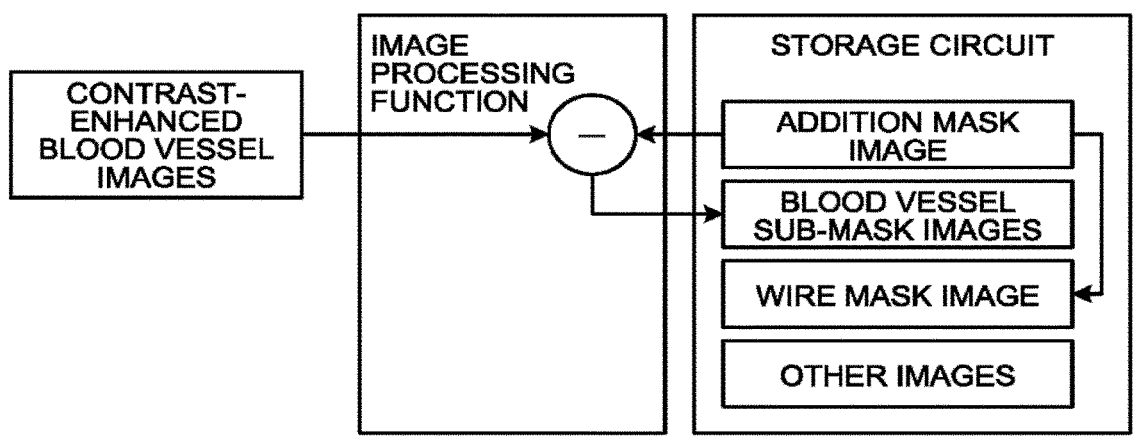
FIG. 13 is a diagram for explaining image data stored in storage according to the fourth embodiment.

In this situation, the wire mask image stored in the storage 24 according to the fourth embodiment is the addition mask image acquired at the time of generating the blood vessel sub-mask image. FIG. 13 is a diagram for explaining the image data stored in the storage 24 according to the fourth embodiment. As illustrated in FIG. 13, the storage 24 according to the fourth embodiment stores therein the addition mask image, the blood vessel sub-mask images, the wire mask image, and other images. In this situation, the addition mask image is an X-ray image acquired at the time of generating the blood vessel sub-mask image, by calculating an arithmetic mean of a plurality of X-ray images acquired while no contrast agent is injected in the subject.

As illustrated in FIG. 13, the image processing function 212 generates the blood vessel sub-mask images by calculating the differences between the contrast-enhanced blood vessel images acquired while a contrast agent is injected in the subject and the addition mask image and stores the generated blood vessel sub-mask images into the storage 24. In this situation, when the addition mask image is acquired under an acquisition condition that is the same as the acquisition condition used in the fluoroscopy roadmap process, the image processing function 212 according to the fourth embodiment stores the addition mask image into the storage 24 as a wire mask image, as illustrated in FIG. 13. For example, when the addition mask image is acquired under a fluoroscopy condition, the image processing function 212 stores the addition mask image into the storage 24 as the wire mask image.

When the fluoroscopy roadmap process is started, the image processing function 212 reads the addition mask image stored in the storage 24 as the wire mask image and sequentially generates difference images by performing a difference calculating process between the sequentially-acquired live images and the read addition mask image. Further, the image processing function 212 sequentially generates fluoroscopy roadmap images, by combining the sequentially-generated difference images with the blood vessel sub-mask image. The controlling function 213 causes the display 23 to sequentially display the fluoroscopy roadmap images that are sequentially generated.

As explained above, the X-ray diagnosis apparatus 100 according to the fourth embodiment is configured so that the storage 24 stores therein the addition mask image as the wire mask image. Further, the image processing function 212 is configured to generate the difference images by using the addition mask image stored as the wire mask image. Accordingly, it is possible to display the fluoroscopy roadmap images that are easy to observe, immediately after the fluoroscopy roadmap process is started.

In the above explanation, the example is explained in which the addition mask image stored in the storage 24 is used as the wire mask image; however, possible embodiments are not limited to this example. It is also possible to combine the fourth embodiment with any of the first to the third embodiments. In the following sections, an example in which the fourth embodiment is combined with the first embodiment will be explained.

In that situation, the image processing function 212 judges whether or not the storage 24 stores therein a wire mask image. When the storage 24 stores a wire mask image therein, the image processing function 212 sequentially generates difference images by performing the difference calculating process between the live images and the addition mask image stored in the storage 24. On the contrary, when the storage 24 stores therein no wire mask image, the image processing function 212 generates a wire mask image by performing the same process as that described in the first embodiment and further generates difference images.

Examples of the situation where the addition mask image is not stored as a wire mask image include, for example, the situation where the addition mask image (and the contrast-enhanced blood vessel images) is acquired by using an image taking condition having a larger radiation amount than that of the fluoroscopy condition. If an image taken under a different image taking condition were used as a wire mask image, the level of precision of the difference calculating process would be degraded. Accordingly, such an image taken under a different image taking condition is not used as a wire mask image.

Figure 14:
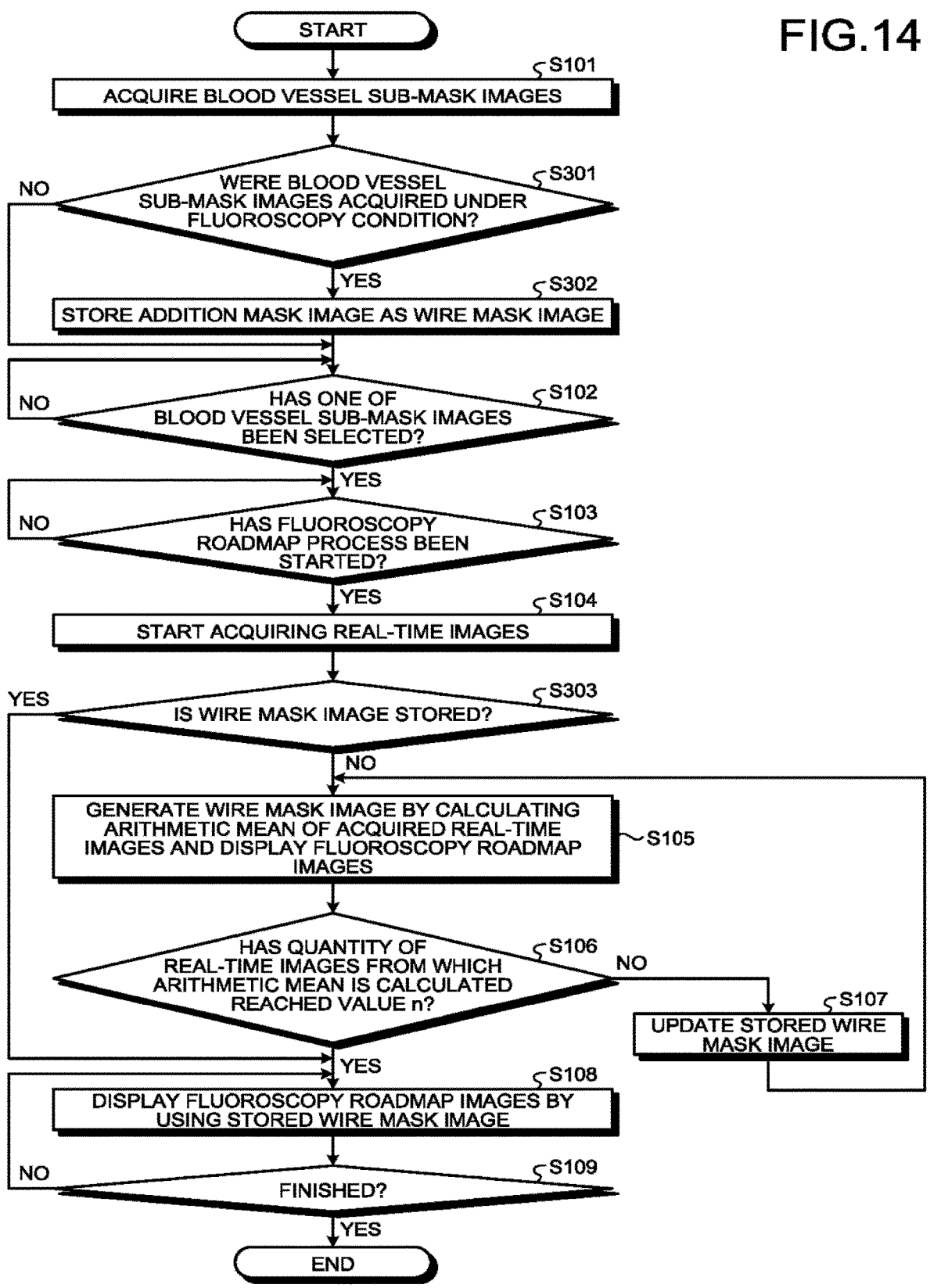
FIG. 14 is a flowchart illustrating a processing procedure performed by the X-ray diagnosis apparatus according to the fourth embodiment.

Next, a process performed by the X-ray diagnosis apparatus 100 according to the fourth embodiment will be explained, with reference to FIG. 14. FIG. 14 is a flowchart illustrating a processing procedure performed by the X-ray diagnosis apparatus 100 according to the fourth embodiment. FIG. 14 illustrates the process performed when the fourth embodiment is combined with the X-ray diagnosis apparatus according to the first embodiment. Further, in FIG. 14, some of the processes that are the same as those in the first embodiment (in FIG. 7) are referred to by using the same reference characters. Steps S301 through S303 in FIG. 14 are steps at which the processing circuitry 21 reads and executes the program corresponding to the image processing function 212 from the storage 24.

For example, as illustrated in FIG. 14, the processing circuitry 21 acquires blood vessel sub-mask images according to an instruction received from the user via the input interface 22 (step S101) and judges whether or not the blood vessel sub-mask images were acquired under a fluoroscopy condition (step S301). When the blood vessel sub-mask images were acquired under a fluoroscopy condition (step S301: Yes), the processing circuitry 21 stores the addition mask image into the storage 24 as a wire mask image (step S302) and judges whether or not one of the blood vessel sub-mask images has been selected (step S102). On the contrary, when the blood vessel sub-mask images were not acquired under a fluoroscopy condition (step S301: No), the processing circuitry 21 judges whether or not one of the blood vessel sub-mask images has been selected (step S102).

When one of the blood vessel sub-mask images has been selected (step S102: Yes), the processing circuitry 21 judges whether or not a fluoroscopy button has been pressed to start the fluoroscopy roadmap process (step S103). On the contrary, until it is determined at step S102 that one of the blood vessel sub-mask images has been selected (step S102: No), the processing circuitry is in a standby state.

When it is determined at step S103 that the fluoroscopy roadmap process is started (step S103: Yes), the processing circuitry 21 starts acquiring real-time images (step S104) and judges whether or not a wire mask image is stored (step S303). When a wire mask image is stored (step S303: Yes), the processing circuitry 21 generates difference images by using the stored wire mask image and further causes fluoroscopy roadmap images to be displayed (step S108).

On the contrary, when no wire mask image is stored (step S303: No), the processing circuitry 21 generates a wire mask image by calculating an arithmetic mean of the acquired real-time images and causes the display 23 to display fluoroscopy roadmap images (step S105). In this situation, until it is determined at step S103 that the fluoroscopy roadmap process is started (step S103: No), the processing circuitry is in a standby state.

Subsequent to step S105, the processing circuitry 21 judges whether or not the quantity of the real-time images from which the arithmetic mean is calculated has reached the predetermined value "n" (step S106). When the quantity has not reached the value "n", the processing circuitry 21 updates the stored wire mask image (step S107) and returns to step S105 where the processing circuitry 21 generates a wire mask image by using the newly-generated real-time image, generates difference images by using the generated wire mask image, and further causes fluoroscopy roadmap images to be displayed.

On the contrary, when it is determined at step S106 that the quantity has reached the value "n", the processing circuitry 21 updates the wire mask image stored in the storage 24 with the wire mask image generated by using the "n" real-time images, also generates difference images by using the stored wire mask image, and further causes fluoroscopy roadmap images to be displayed (step S108).

After that, the processing circuitry 21 judges whether or not the fluoroscopy roadmap process is finished (step S109). When the fluoroscopy roadmap process is not finished (step S109: No), the processing circuitry 21 generates difference images by using the newly-acquired real-time image and the stored wire mask image and further causes fluoroscopy roadmap images to be displayed. In this situation, until it is determined at step S109 that the fluoroscopy roadmap process is finished, the fluoroscopy roadmap process using the stored wire mask image is continued.

As explained above, according to the fourth embodiment, the acquiring function 211 is configured to acquire the addition mask image used for generating the blood vessel sub-mask images. Further, the acquiring function 211 is configured to sequentially acquire the live images that are substantially in the same position as the blood vessel sub-mask images. The image processing function 212 is configured to sequentially generate the difference images by performing the difference calculating process between the live images and the addition mask image. Consequently, the X-ray diagnosis apparatus 100 according to the fourth embodiment makes it possible to display the fluoroscopy roadmap images that are easy to observe, immediately after the fluoroscopy roadmap process is started.

Further, according to the fourth embodiment, the storage 24 is configured to store therein the addition mask image used for generating the blood vessel sub-mask images that are substantially in the same position as the live images, as the wire mask image. When no addition mask image is stored in the storage 24, the image processing function 212 generates a wire mask image. On the contrary, when the addition mask image is stored in the storage 24, the image processing function 212 sequentially generates the difference images by performing the difference calculating process between the live images and the addition mask image stored in the storage 24. Consequently, the X-ray diagnosis apparatus 100 according to the fourth embodiment makes is possible, when the addition mask image is stored as the wire mask image, to display the fluoroscopy roadmap images that are easy to observe, immediately after the fluoroscopy roadmap process is started.

Fifth Embodiment

In a fifth embodiment, disregarding the wire mask image stored in the storage 24 and re-generating a wire mask image will be explained. In the following sections, some of the constituent elements that are the same as those explained in the first embodiment will be referred to by using the same reference characters, and the explanations thereof may be omitted.

When the acquisition condition of the live images is changed, the image processing function 212 according to the fifth embodiment is configured to delete the wire mask image stored in the storage 24 and to re-generate a wire mask image by using a plurality of live images obtained after the acquisition condition is changed. For example, as being triggered by the acquisition condition of the live images being changed, the image processing function 212 deletes the wire mask image stored in the storage 24 and re-generates a wire mask image by using the plurality of live images obtained after the acquisition condition is changed. Alternatively, for example, as being triggered by acquisition of live images being newly started under a post-change acquisition condition, the image processing function 212 deletes the wire mask image stored in the storage 24 and re-generates a wire mask image by using the plurality of live images obtained after the acquisition condition is changed.

In that situation, for example, through Controller Area Network (CAN) communication or the like, the image processing function 212 obtains, in a real-time manner, position information of the C-arm 15 and the table 14, as well as opening-degree information of the collimator blades included in the X-ray collimator 13, information about a Field Of View (FOV) (the size of the field of view), and the like. In the following sections, these pieces of information will collectively be referred to as C-arm position information. In this situation, the position of the C-arm 15 includes a subject-table angle, a Source-Intensifier Distance (SID), and the like. The position information of the table 14 includes the height of the table, the lengthwise slide position, the widthwise slide position, and the like.

The image processing function 212 stores therein the C-arm position information corresponding to substantially the same time as when the wire mask image is generated. Further, the image processing function 212 exercises control so as to discard the wire mask image when the current C-arm position information or the like is different from the stored C-arm position information by an amount exceeding a certain range. Further, when the wire mask image has been discarded, the image processing function 212 generates a wire mask image again, by using the method described in the first embodiment, for example.

For instance, when the FOV is changed while the live images are being acquired, the image processing function 212 discards the stored wire mask image and re-generates a wire mask image. In another example, the image processing function 212 stores therein the positions of the collimator blades corresponding to the time when the stored wire mask image is generated and, when the collimator blades have moved by an amount exceeding a certain range while the live images are being acquired, the image processing function 212 discards the stored wire mask image and re-generates a wire mask image.

In yet another example, the image processing function 212 does not discard the wire mask image until the user releases the fluoroscopy switch, and when the fluoroscopy switch is pressed again, the image processing function 212 discards the wire mask image and generates a wire mask image again by using the method explained in the first embodiment, for example. In yet another example, after the FOV is changed, the image processing function 212 discards the wire mask image that is stored when the next fluoroscopy process is started and re-generates a wire mask image. In yet another example, the image processing function 212 stores therein the positions of the collimator blades corresponding to the time when the stored wire mask image is generated and, when the collimator blades have moved by an amount exceeding a certain range, the image processing function 212 discards the wire mask image that is stored when the next fluoroscopy process is started and re-generates a wire mask image. Alternatively, the image processing function 212 may discard the wire mask image when the FOV or the positions of the collimator blades have changed while the live images are being acquired and re-generate a wire mask image when the next fluoroscopy process is started.

Figure 15:
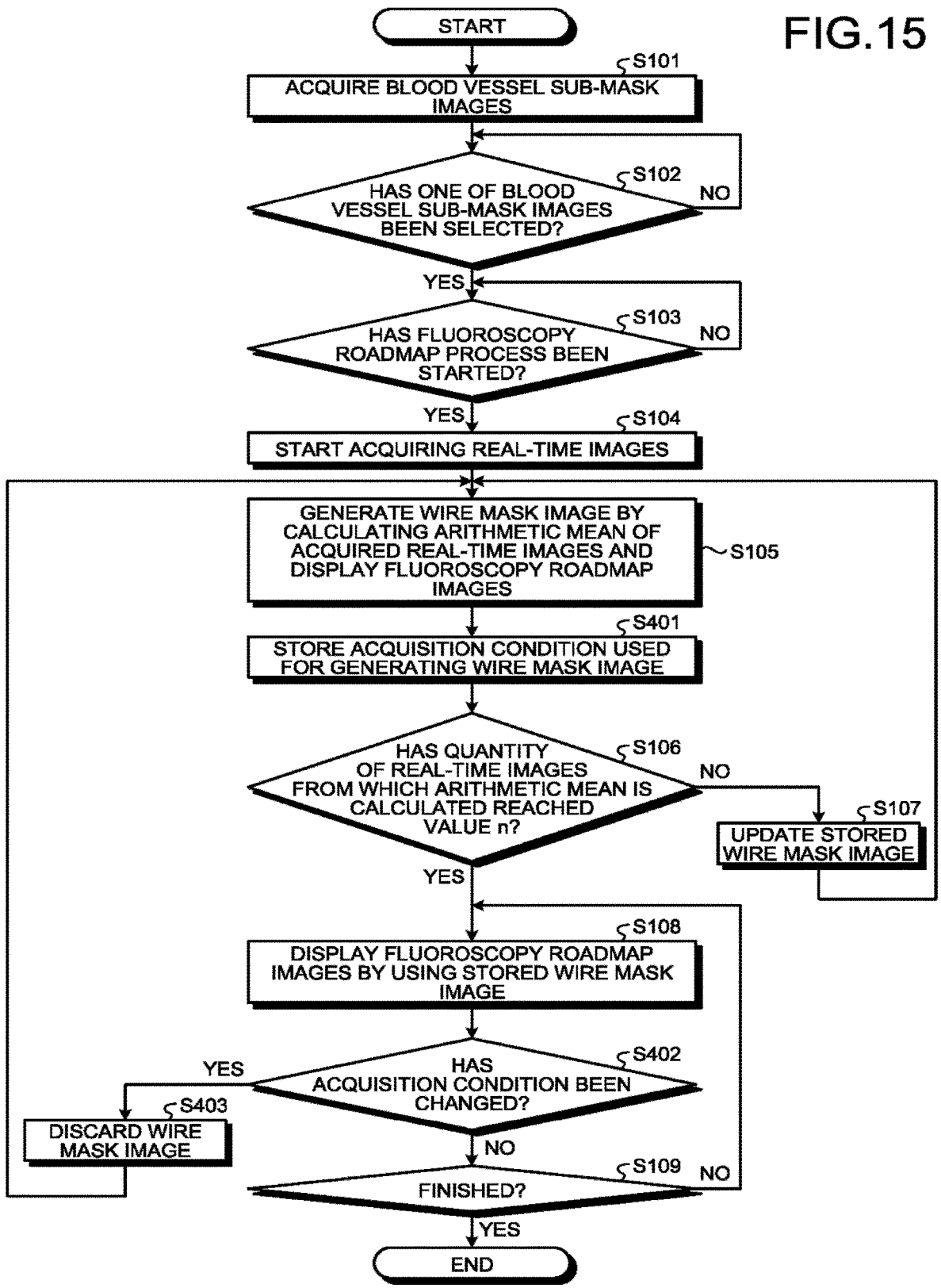
FIG. 15 is a flowchart illustrating a processing procedure performed by an X-ray diagnosis apparatus according to a fifth embodiment.

Next, a process performed by the X-ray diagnosis apparatus 100 according to the fifth embodiment will be explained, with reference to FIG. 15. FIG. 15 is a flowchart illustrating a processing procedure performed by the X-ray diagnosis apparatus 100 according to the fifth embodiment. FIG. 15 illustrates an example in which, as being triggered by the acquisition condition of the live images being changed, the wire mask image is discarded and a wire mask image is re-generated during the acquisition. Further, in FIG. 15, some of the processes that are the same as those in the first embodiment (in FIG. 7) are referred to by using the same reference characters. Steps S401 through S403 in FIG. 15 are steps at which the processing circuitry 21 reads and executes the program corresponding to the image processing function 212 from the storage 24.

For example, as illustrated in FIG. 15, the processing circuitry 21 acquires blood vessel sub-mask images according to an instruction received from the user via the input interface 22 (step S101) and judges whether or not a blood vessel sub-mask image to be used for a fluoroscopy roadmap process has been selected from among the acquired blood vessel sub-mask images (step S102). When one of the blood vessel sub-mask images has been selected (step S102: Yes), the processing circuitry 21 judges whether or not a fluoroscopy button has been pressed to start the fluoroscopy roadmap process (step S103). On the contrary, until it is determined at step S102 that one of the blood vessel sub-mask images has been selected (step S102: No), the processing circuitry is in a standby state.

When it is determined at step S103 that the fluoroscopy roadmap process is started (step S103: Yes), the processing circuitry 21 starts acquiring real-time images (step S104), generates a wire mask image by calculating an arithmetic mean of the acquired real-time images, and further causes the display 23 to display fluoroscopy roadmap images (step S105). On the contrary, until it is determined at step S103 that the fluoroscopy roadmap process is started (step S103: No), the processing circuitry is in a standby state.

Subsequent to step S105, the processing circuitry 21 stores therein the acquisition condition used when the wire mask image is generated (step S401) and judges whether or not the quantity of the real-time images from which the arithmetic mean is calculated has reached the predetermined value "n" (step S106). When the quantity has not reached the value "n", the processing circuitry 21 updates the stored wire mask image (step S107) and returns to step S105 where the processing circuitry 21 generates a wire mask image by using the newly-generated real-time image, generates difference images by using the generated wire mask image, and further causes fluoroscopy roadmap images to be displayed.

On the contrary, when it is determined at step S106 that the quantity has reached the value "n", the processing circuitry 21 updates the wire mask image stored in the storage 24 with the wire mask image generated by using the "n" real-time images, also generates difference images by using the stored wire mask image, and further causes fluoroscopy roadmap images to be displayed (step S108).

After that, the processing circuitry 21 judges whether or not the acquisition condition has been changed (step S402). When the acquisition condition has been changed (step S402: Yes), the processing circuitry 21 discards the wire mask image (step S403) and returns to step S105 where the processing circuitry 21 generates a wire mask image by using the newly-generated real-time image, generates difference images by using the generated wire mask image, and further causes fluoroscopy roadmap images to be displayed.

On the contrary, when the acquisition condition has not bee changed (step S402: No), the processing circuitry 21 judges whether or not the fluoroscopy roadmap process is finished (step S109). When the fluoroscopy roadmap process is not finished (step S109: No), the processing circuitry 21 generates difference images by using the newly-acquired real-time image and the stored wire mask image and further causes fluoroscopy roadmap images to be displayed. In this situation, until it is determined at step S109 that the fluoroscopy roadmap process is finished, the process of judging whether or not the acquisition condition has been changed and the fluoroscopy roadmap process using the stored wire mask image are continued.

As explained above, according to the fifth embodiment, when the acquisition condition of the live images has been changed, the image processing function 212 is configured to delete the wire mask image stored in the storage 24 and to re-generate the wire mask image by using the plurality of live images obtained after the acquisition condition is changed. Consequently, the X-ray diagnosis apparatus 100 according to the fifth embodiment makes it possible to perform the fluoroscopy roadmap process compliant with the change of the acquisition condition.

Further, in the fifth embodiment, as being triggered by the change of the acquisition condition used for acquiring the live images, the image processing function 212 is configured to delete the wire mask image stored in the storage 24 and to re-generate the wire mask image by using the plurality of live images obtained after the acquisition condition is changed. Consequently, the X-ray diagnosis apparatus 100 according to the fifth embodiment makes it possible to promptly comply even with the change of the acquisition condition.

Further, in the fifth embodiment, as being triggered by the acquisition of the live images being newly started under the post-change acquisition condition, the image processing function 212 is configured to delete the wire mask image stored in the storage 24 and to re-generate the wire mask image by using the plurality of live images obtained after the acquisition condition is changed. Consequently, the X-ray diagnosis apparatus 100 according to the fifth embodiment is able to re-generate the wire mask image after the change of the acquisition condition is confirmed.

Sixth Embodiment

The first to the fifth embodiments have thus been explained. It is, however, also possible to carry out the present disclosure in various different modes other than those described above in the first to the fifth embodiments.

Figure 16:
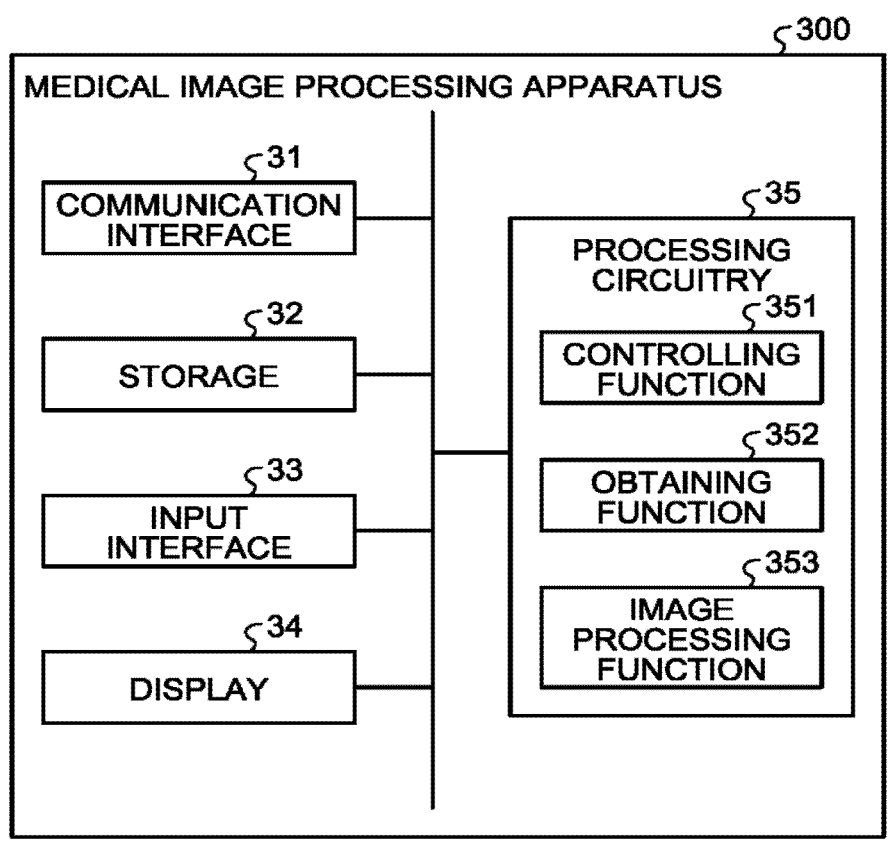
FIG. 16 is diagram illustrating an exemplary configuration of a medical image processing apparatus according to a sixth embodiment.

In the embodiments described above, the examples are explained in which the X-ray diagnosis apparatus 100 performs the processes; however, possible embodiments are not limited to those examples. For instance, another arrangement is also acceptable in which a medical image processing apparatus obtains X-ray images from the X-ray diagnosis apparatus 100 and performs the processes described above. FIG. 16 is a diagram illustrating an exemplary configuration of a medical image processing apparatus 300 according to a sixth embodiment. As illustrated in FIG. 16, the medical image processing apparatus 300 includes a communication interface 31, storage 32, an input interface 33, a display 34, and processing circuitry 35.

The communication interface 31 is connected to the processing circuitry 35 and is configured to control transfer and communication of various types of data to and from the X-ray diagnosis apparatus 100 that is connected via a network. For example, the communication interface 31 is realized by using a network card, a network adaptor, a Network Interface Controller (NIC), or the like. In the present embodiment, the communication interface 31 is configured to receive X-ray images from the X-ray diagnosis apparatus 100 and to output the received X-ray images to the processing circuitry 35. In this situation, the communication interface 31 is capable of receiving the real-time X-ray images acquired by the X-ray diagnosis apparatus 100 and outputting the received X-ray images to the processing circuitry 35.

The storage 32 is connected to the processing circuitry 35 and is configured to store therein various types of data. For example, the storage 32 is realized by using a semiconductor memory element such as a Random Access Memory (RAM), a flash memory, or the like, or a hard disk, an optical disk, or the like. In the present embodiment, the storage 32 is configured to stores therein the X-ray images received from the X-ray diagnosis apparatus 100 and X-ray images generated by the processing circuitry 35. For example, the storage 32 stores therein contrast-enhanced blood vessel images, non-contrast-enhanced blood vessel images (addition mask images), blood vessel sub-mask images, wire mask images, difference images, combined images (fluoroscopy roadmap images), and the like. Further, the storage 32 is configured to store therein various types of information used in processes performed by the processing circuitry 35, processing results obtained by the processing circuitry 35, and the like.

The input interface 33 is realized by using a trackball, a switch button, a mouse, a keyboard, a touchpad used for performing an input operation by touching an operation surface thereof, a touch screen in which a display screen and a touchpad are integrally formed, a contactless input circuit using an optical sensor, an audio input circuit, and/or the like used for establishing various settings and the like.

The input interface 33 is connected to the processing circuitry 35 and is configured to convert an input operation received from the operator into an electrical signal and to output the electrical signal to the processing circuitry 35. The input interface 33 of the present disclosure does not necessarily have to include one or more physical operation component parts such as a mouse and a keyboard. For example, possible examples of the input interface include a processing circuitry configured to receive an electrical signal corresponding to an input operation from an external input device provided separately from the apparatus and to output the electrical signal to a controlling circuitry.

The display 34 is connected to the processing circuitry 35 and is configured to display various types of information and various types of images output from the processing circuitry 35. For example, the display 34 is realized by using a liquid crystal monitor, a Cathode Ray Tube (CRT) monitor, a touch panel, or the like. For example, the display 34 is configured to display a Graphical User Interface (GUI) used for receiving an instruction from the operator, various types of images, and various types of processing results obtained by the processing circuitry 35.

According to an input operation received from the operator via the input interface 33, the processing circuitry 35 is configured to control constituent elements of the medical image processing apparatus 300. For example, the processing circuitry 35 is realized by using a processor. In the present embodiment, the processing circuitry 35 is configured to store the X-ray images output from the communication interface 31 into the storage 32. Further, the processing circuitry 35 is configured to read any of the X-ray images from the storage 32 and to cause the display 34 to display combined images generated by using the read X-ray images.

As illustrated in FIG. 16, the processing circuitry 35 is configured to execute, for example, a controlling function 351, an obtaining function 352, and an image processing function 353. In this situation, for example, processing functions performed by the constituent elements of the processing circuitry 35 illustrated in FIG. 16, namely, the controlling function 351, the obtaining function 352, and the image processing function 353 are recorded in the storage 32 in the form of computer-executable programs. For example, the processing circuitry 35 is a processor and is configured to read and execute the programs from the storage 32 so as to realize the functions corresponding to the read programs. In other words, the processing circuitry 35 that has read the programs has the functions illustrated within the processing circuitry 35 in FIG. 16.

The controlling function 351 is configured to control the entirety of the medical image processing apparatus 300 and to perform the same processes as those performed by the controlling function 213 explained above. The obtaining function 352 is an example of an X-ray image obtaining unit and is configured to obtain the X-ray images from the X-ray diagnosis apparatus 100 and to perform the same processes as those performed by the acquiring function 211 explained above. The image processing function 353 is configured to perform the same processes as those performed by the image processing function 212 explained above.

In the embodiments described above, the examples are explained in which the single processing circuit (the processing circuitry 21 and the processing circuitry 35) realizes the processing functions; however, possible embodiments are not limited to those examples. For instance, the processing circuitry 21 (and the processing circuitry 35) may be structured by combining together a plurality of independent processors, so that the processing functions are realized as a result of the processors executing the programs. Further, the processing functions of the processing circuitry 21 (and the processing circuitry 35) may be realized as being integrated into a single processing circuit or distributed among a plurality of processing circuits, as appropriate.

The term "processor" used in the above explanation denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions by reading and executing the programs saved in the storage 24 (or the storage 32). In this situation, instead of saving the programs in the storage 24 (or the storage 32), it is also acceptable to directly incorporate the programs in the circuits of the processors. In that situation, the processors realize the functions thereof by reading and executing the programs incorporated in the circuits thereof. The processors in the present embodiments do not each necessarily have to be structured as a single circuit. It is also acceptable to structure one processor by combining together a plurality of independent circuits so as to realize the functions thereof.

In this regard, a medical image processing computer program (hereinafter, "medical image processing program") executed by the one or more processors is provided as being incorporated in a Read-Only Memory (ROM), a storage unit, or the like. The medical image processing program may be provided as being stored in a computer-readable storage medium such as a Compact Disk Read-Only Memory (CD-ROM), a Flexible Disk (FD), a Compact Disk Recordable (CD-R), a Digital Versatile Disk (DVD), or the like, in a file in such a format that is either installable or executable for the devices. Further, the medical image processing program may be stored in a computer connected to a network such as the Internet, so as to be provided or distributed as being downloaded via the network. For example, the medical image processing program is structured with modules including the functional units described below. In the actual hardware, as a result of a CPU reading and executing the program from a storage medium such as a ROM, the modules are loaded into a main storage device so as to be generated in the main storage device.

Further, the constituent elements of the apparatuses and the devices illustrated in the drawings in the above embodiments are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program that is analyzed and executed by the CPU or may be realized as hardware using wired logic.

As explained above, according to at least one aspect of the embodiments, it is possible to improve the sense of operability of the fluoroscopy roadmap function.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry configured to
sequentially obtain X-ray images;
sequentially generate, every time a new X-ray image is obtained after a start of the obtainment of the X-ray images, average images by using the obtained plurality of X-ray images including the new X-ray image, in parallel to the obtainment of the X-ray images; and
sequentially generate difference images by performing a difference calculating process between the X-ray images and the average images, in parallel to the obtainment of the X-ray images and the generation of the average images.

2. The medical image processing apparatus according to claim 1, wherein the processing circuitry is further configured to
sequentially generate combined images by combining the difference images with a blood vessel image that is substantially in a same position as the X-ray images, and
exercise control so as to cause the combined images to be sequentially displayed.

3. The medical image processing apparatus according to claim 1, wherein
when a quantity of the X-ray images used for generating any one of the average images has reached a value, the processing circuitry is configured to stop generating the average images and store, into a storage, the average image generated by using the X-ray images of which the quantity is equal to the value, and
the processing circuitry is configured to perform a difference calculating process using the average image stored in the storage, on X-ray images obtained while exceeding the value.

4. The medical image processing apparatus according to claim 3, wherein, when an acquisition condition of the X-ray images is changed, the processing circuitry is configured to delete the average image stored in the storage and re-generate an average image by using a plurality of X-ray images obtained after the acquisition condition is changed.

5. The medical image processing apparatus according to claim 4, wherein, being triggered by the acquisition condition of the X-ray images being changed, the processing circuitry is configured to delete the average image stored in the storage and re-generate an average image by using a plurality of X-ray images obtained after the acquisition condition is changed.

6. The medical image processing apparatus according to claim 4, wherein, being triggered by acquisition of X-ray images being newly started under a post-change acquisition condition, the processing circuitry is configured to delete the average image stored in the storage and re-generate an average image by using a plurality of X-ray images obtained after the acquisition condition is changed.

7. The medical image processing apparatus according to claim 1, wherein
when a quantity of the obtained X-ray images has reached a first value, the processing circuitry is configured to stop generating the average images and store, into a storage, an average image generated by using X-ray images that are among the X-ray images of which the quantity is equal to the first value and of which a quantity is equal to a second value as counted from a most recent X-ray image, and
the processing circuitry is configured to perform a difference calculating process using the average image stored in the storage, on X-ray images obtained while exceeding the first value.

8. The medical image processing apparatus according to claim 1, wherein the processing circuitry is configured to further exercise control so that a framerate used for acquiring the X-ray images is relatively higher for a time period during which the average images are generated.

9. The medical image processing apparatus according to claim 1, further comprising a storage configured to store therein, as at least one of the average images, a non-contrast-enhanced blood vessel image that was used for generating a blood vessel image being substantially in a same position as the X-ray images, wherein
when the non-contrast-enhanced blood vessel image is not stored in the storage, the processing circuitry is configured to generate the average images, and
when the non-contrast-enhanced blood vessel image is stored in the storage, the processing circuitry is configured to sequentially generate the difference images by performing the difference calculating process between the obtained X-ray images and the non-contrast-enhanced blood vessel image stored in the storage.

10. A medical image processing apparatus comprising:
processing circuitry configured to
obtain a non-contrast-enhanced blood vessel image that was used for generating a blood vessel image;
sequentially obtain X-ray images that are substantially in a same position as a contrast-enhanced blood vessel image that was used for generating the blood vessel image, the X-ray images being images acquired when a medical device is inserted into a blood vessel; and
sequentially generate difference images by performing a difference calculating process between the X-ray images and the non-contrast-enhanced blood vessel image, in parallel to the obtainment of the X-ray images.

11. An X-ray diagnosis apparatus comprising:
processing circuitry configured to
sequentially acquire X-ray images;
sequentially generate, every time a new X-ray image is acquired after a start of acquisition of the X-ray images, average images by using the acquired plurality of X-ray images including the new X-ray image, in parallel to the acquisition of the X-ray images; and
sequentially generate difference images by performing a difference calculating process between the X-ray images and the average images, in parallel to the acquisition of the X-ray images and the generation of the average images.

12. An X-ray diagnosis apparatus comprising:
processing circuitry configured to
acquire a non-contrast-enhanced blood vessel image that was used for generating a blood vessel image, the X-ray images being images acquired when a medical device is inserted into a blood vessel;
sequentially acquire X-ray images that are substantially in a same position as a contrast-enhanced blood vessel image that was used for generating the blood vessel image; and
sequentially generate difference images by performing a difference calculating process between the X-ray images and the non-contrast-enhanced blood vessel image, in parallel to the obtainment of the X-ray images.

13. A medical image processing method comprising:
sequentially obtaining X-ray images;
sequentially generating, every time a new X-ray image is obtained after a start of the obtainment of the X-ray images average images by using the obtained plurality of X-ray images including the new X-ray image, in parallel to the obtainment of the X-ray images; and
sequentially generating difference images by performing a difference calculating process between the X-ray images and the average images, in parallel to the obtainment of the X-ray images and the generation of the average images.

14. The medical image processing method according to claim 13, comprising acquiring the X-ray images at a framerate relatively higher for a time period during which the average images are generated.

15. The medical image processing method according to claim 13, further comprising storing, as at least one of the average images, a non-contrast-enhanced blood vessel image that was used for generating a blood vessel image being substantially in a same position as the X-ray images, wherein
when the non-contrast-enhanced blood vessel image is not stored, generating the average images, and
when the non-contrast-enhanced blood vessel image is stored, sequentially generating the difference images by performing the difference calculating process between the obtained X-ray images and the stored non-contrast-enhanced blood vessel image.

16. The medical image processing method according to claim 13, comprising:
when a quantity of the X-ray images used for generating any one of the average images has reached a value, stopping generation of the average images and storing, the average image generated by using the X-ray images of which the quantity is equal to the value, and performing a difference calculating process using the stored average image, on X-ray images obtained while exceeding the value; and
when an acquisition condition of the X-ray images is changed, deleting the average image stored and re-generate an average image by using a plurality of X-ray images obtained after the acquisition condition is changed.

17. The medical image processing method according to claim 16, comprising, when triggered by the acquisition condition of the X-ray images being changed, deleting the stored average image and re-generating an average image by using a plurality of X-ray images obtained after the acquisition condition is changed.

18. The medical image processing method according to claim 16, comprising, when triggered by acquisition of X-ray images being newly started under a post-change acquisition condition, deleting the stored average image and re-generating an average image by using a plurality of X-ray images obtained after the acquisition condition is changed.

19. A medical image processing method comprising:
obtaining a non-contrast-enhanced blood vessel image that was used for generating a blood vessel image;
sequentially obtaining X-ray images that are substantially in a same position as a contrast-enhanced blood vessel image that was used for generating the blood vessel image, the X-ray images being images acquired when a medical device is inserted into a blood vessel; and
sequentially generating difference images by performing a difference calculating process between the X-ray images and the non-contrast-enhanced blood vessel image in parallel to the obtainment of the X-ray images.

* * * * *